(12) United States Patent
Smith

(10) Patent No.: US 11,822,044 B2
(45) Date of Patent: Nov. 21, 2023

(54) COMPACT BODY SCANNER

(71) Applicant: TEK84 INC., Poway, CA (US)

(72) Inventor: Steven Winn Smith, San Diego, CA (US)

(73) Assignee: TEK84 INC., Poway, CA (US)

( * ) Notice: Subject to any disclaimer, the term of this patent is extended or adjusted under 35 U.S.C. 154(b) by 0 days.

(21) Appl. No.: 18/109,137

(22) Filed: Feb. 13, 2023

(65) Prior Publication Data

US 2023/0184988 A1 Jun. 15, 2023

Related U.S. Application Data

(63) Continuation of application No. 16/911,735, filed on Jun. 25, 2020, which is a continuation-in-part of application No. 16/573,714, filed on Sep. 17, 2019, now Pat. No. 10,705,245, and a continuation-in-part of application No. 16/573,681, filed on Sep. 17, 2019, now Pat. No. 10,705,244, said application No. 16/573,714 is a continuation of application No. 16/246,405, filed on Jan. 11, 2019, now Pat. No. 10,481,295, said application No. 16/573,681 is a
(Continued)

(51) Int. Cl.
*G01V 5/00* (2006.01)
*A61B 6/00* (2006.01)

(52) U.S. Cl.
CPC .......... *G01V 5/0066* (2013.01); *A61B 6/4452* (2013.01); *G01V 5/0016* (2013.01)

(58) Field of Classification Search
None
See application file for complete search history.

(56) References Cited

U.S. PATENT DOCUMENTS

| 5,404,387 A | 4/1995 | Hammond et al. |
| 6,102,567 A | 8/2000 | Cabral et al. |
| 7,016,473 B1 | 3/2006 | Linev et al. |

(Continued)

FOREIGN PATENT DOCUMENTS

| EP | 1189537 | 3/2002 |
| EP | 1257203 | 11/2002 |

(Continued)

OTHER PUBLICATIONS

International Search Report and Written Opinion dated May 7, 2019 for International Application No. PCT/US2019/013369, filed Jan. 11, 2019.

(Continued)

*Primary Examiner* — Hoon K Song
(74) *Attorney, Agent, or Firm* — Sheppard, Mullin, Richter & Hampton LLP

(57) ABSTRACT

Imaging systems and methods are provided for detecting object that may be hidden under clothing, ingested, inserted, or otherwise concealed on or in a person's body. An imaging assembly and mechanisms for vertically moving the imaging assembly may be configured to reduce the overall form factor of such imaging systems, while still retaining an ability to perform full/complete imaging of a subject. A calibration system assembly can be included, comprising a first calibration assembly and second calibration assembly to perform fine-grained adjustments to the positioning of the X-ray detector.

24 Claims, 19 Drawing Sheets

Related U.S. Application Data continuation of application No. 16/246,405, filed on Jan. 11, 2019, now Pat. No. 10,481,295.

(60) Provisional application No. 62/709,213, filed on Jan. 11, 2018.

(56) References Cited

U.S. PATENT DOCUMENTS

| | | | |
|---|---|---|---|
| 9,277,897 B1 * | 3/2016 | Linev | A61B 6/4078 |
| 9,689,811 B2 | 6/2017 | Cox et al. | |
| 9,968,314 B1 | 5/2018 | Sebring | |
| 10,845,500 B2 | 11/2020 | Smith | |
| 2005/0053186 A1 | 3/2005 | Sukovic et al. | |
| 2010/0034451 A1 | 2/2010 | Hughes | |
| 2012/0093288 A1 | 4/2012 | Mastronardi et al. | |
| 2014/0139215 A1 | 5/2014 | Gregerson et al. | |
| 2015/0282776 A1 | 10/2015 | Shin et al. | |
| 2016/0247341 A1 | 8/2016 | Talwerdi | |
| 2016/0252646 A1 | 9/2016 | Sarraiocco | |
| 2017/0071560 A1 | 3/2017 | Gregerson et al. | |
| 2017/0357857 A1 | 12/2017 | Perron | |
| 2017/0365118 A1 | 12/2017 | Nurbegovic | |
| 2018/0149766 A1 | 5/2018 | Singh | |
| 2019/0113652 A1 * | 4/2019 | Allen | A61B 6/50 |
| 2019/0120996 A1 | 4/2019 | Columbri | |
| 2019/0282185 A1 | 9/2019 | Gregerson et al. | |

FOREIGN PATENT DOCUMENTS

| | | |
|---|---|---|
| WO | WO 2001/000092 | 1/2001 |
| WO | WO 2001/060258 | 8/2001 |
| WO | WO 2003/081220 | 10/2003 |

OTHER PUBLICATIONS

Office Action dated Jul. 19, 2021 for Eurasian Application No. 202091681.

Extended European Search Report dated Jul. 22, 2021 for European Application No. 19738324.3.

International Search Report and Written Opinion dated Oct. 19, 2021 for International Application No. PCT/US2021/038945, filed Jun. 24, 2021.

Eurasian Office Action dated Mar. 29, 2022 for Eurasian Application No. 202091681.

Notice of Readiness of Grant dated Aug. 29, 2022 for Eurasian Application No. 202091681.

Non-final Office Action dated Sep. 20, 2022 for U.S. Appl. No. 17/496,401.

Final Office Action dated Apr. 27, 2023 for U.S. Appl. No. 17/496,401, filed Oct. 7, 2021.

Non-final Office Action dated Jun. 21, 2023 for U.S. Appl. No. 18/110,297, filed Feb. 15, 2023.

Non-final Office Action dated Aug. 16, 2023 for U.S. Appl. No. 17/496,401.

* cited by examiner

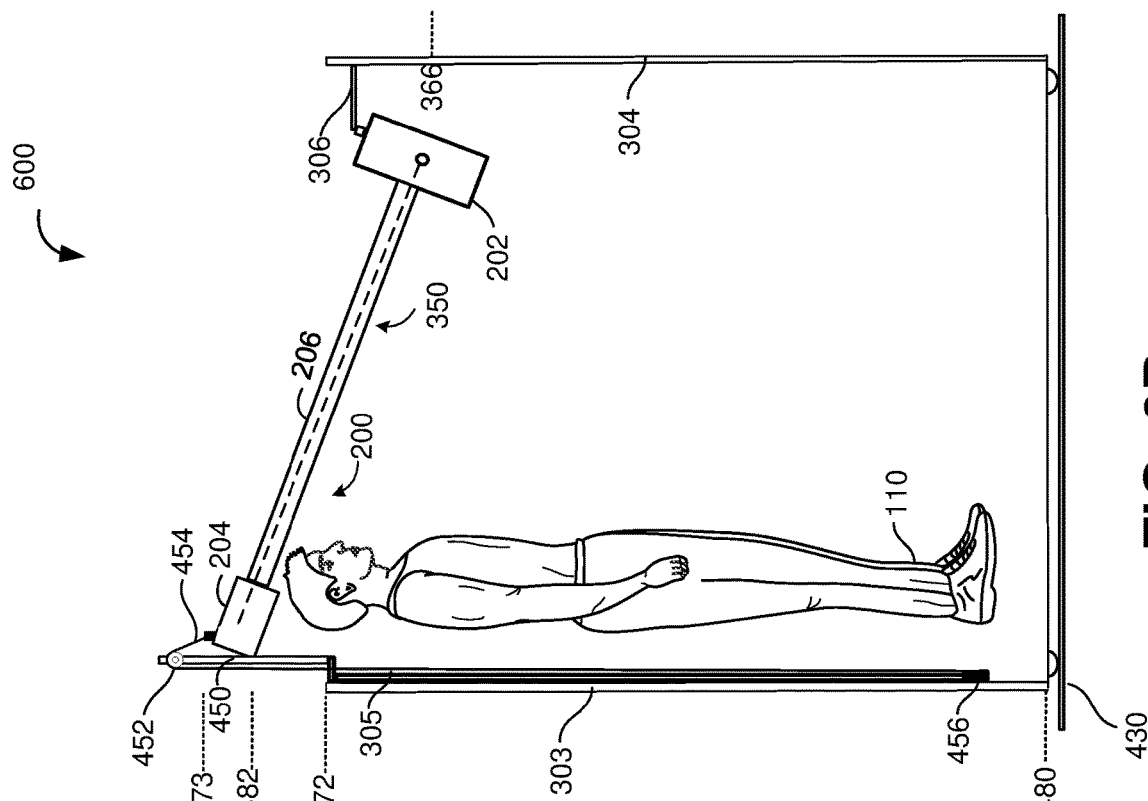
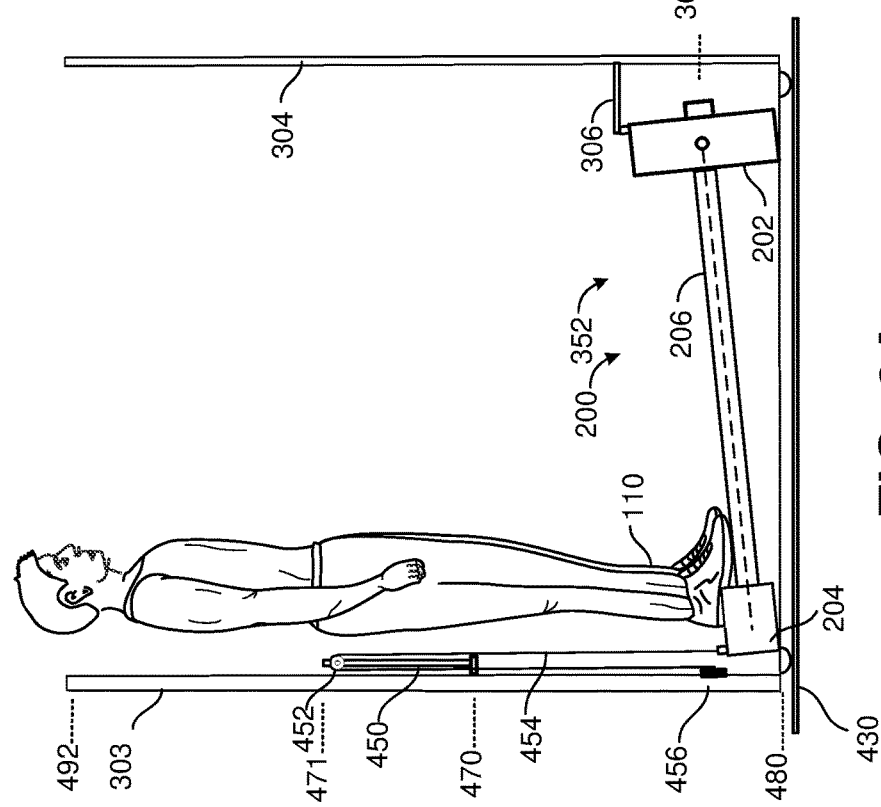
FIG. 6B
FIG. 6A

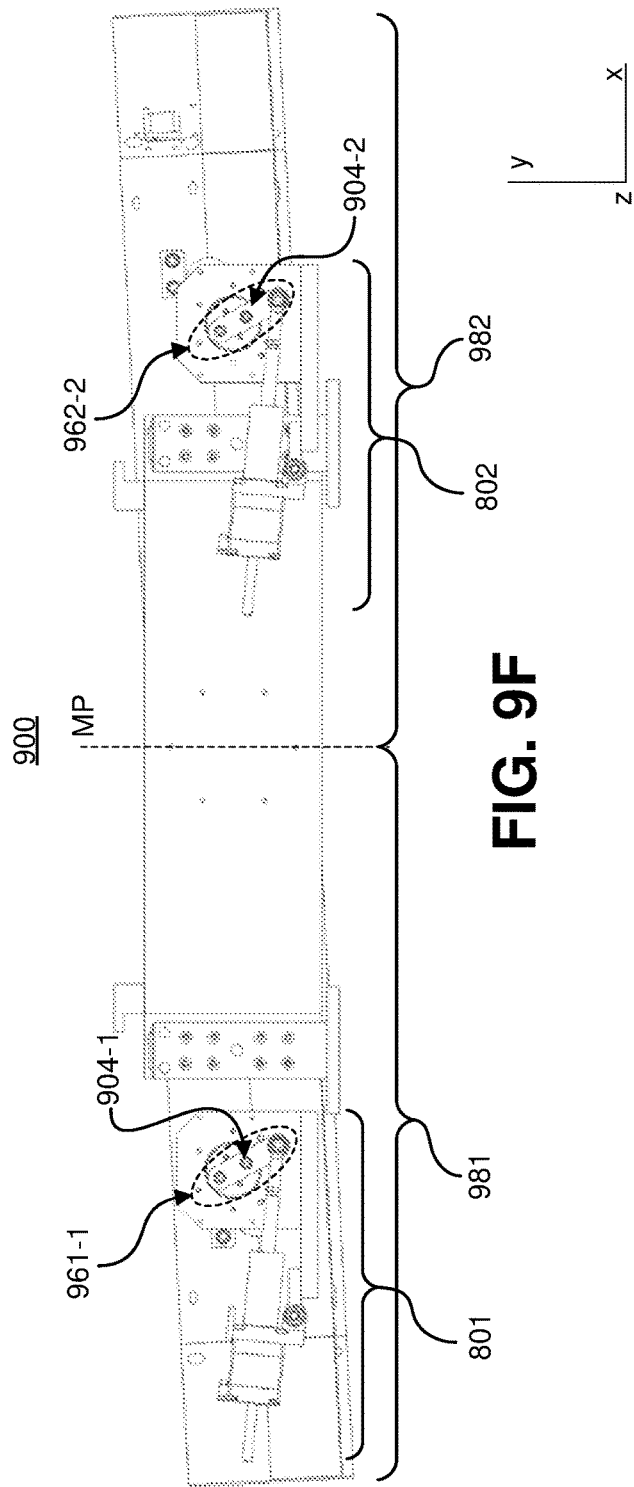
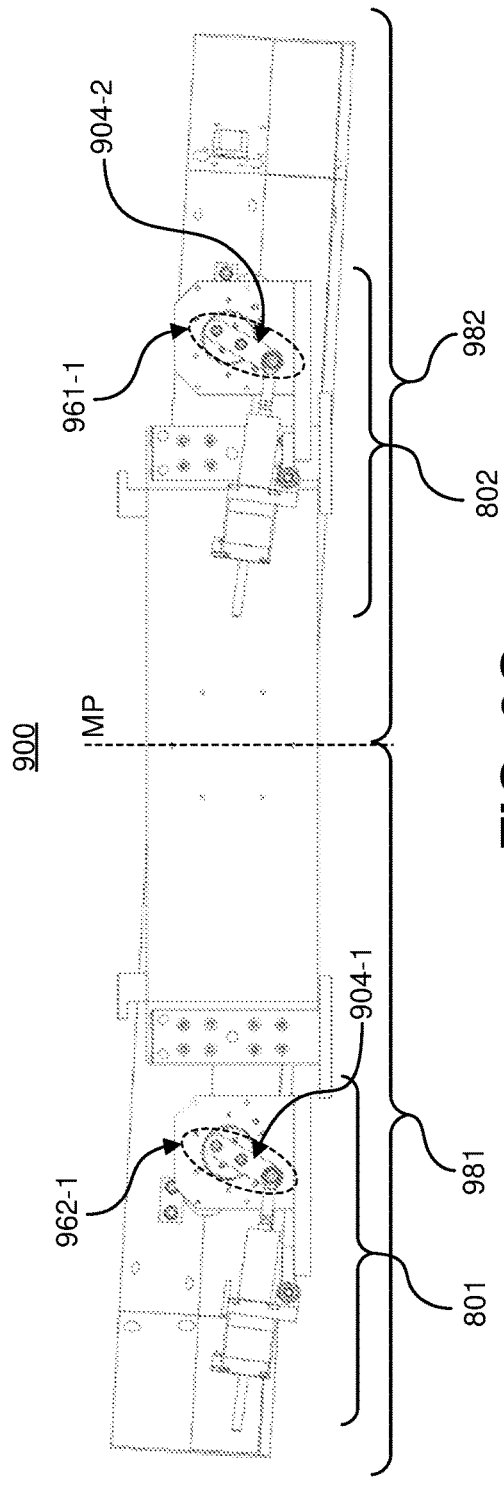

COMPACT BODY SCANNER

CROSS-REFERENCE TO RELATED APPLICATIONS

The present application is a continuation of U.S. patent application Ser. No. 16/911,735, filed Jun. 25, 2020, which is a continuation-in-part of U.S. patent application Ser. No. 16/573,714 filed Sep. 17, 2019, and U.S. patent application Ser. No. 16/573,681 filed Sep. 17, 2019, which are each continuations of U.S. patent application Ser. No. 16/246,405 filed Jan. 11, 2019, which claims the benefit of U.S. Provisional Patent Application No. 62/709,213 filed Jan. 11, 2018, which are hereby incorporated herein by reference in their entireties.

TECHNICAL FIELD

The present disclosure is generally related to radiant energy imaging. More particularly, the present disclosure is directed to imaging systems that use electromagnetic radiation to detect concealed security threats.

BACKGROUND

Criminals and terrorists frequently conceal security threats, such as weapons, explosives, contraband, illicit drugs, under their clothing and in body cavities, when entering security-controlled areas. These security threats must be detected on persons entering such high security areas as prisons, airports, government buildings, nuclear power plants, military bases, and the like. However, searching individuals by hand is time consuming, often ineffective, and objectionable to both the person being screened and the security officer performing the screening.

BRIEF DESCRIPTION OF THE DRAWINGS

FIGS. 6A-6B illustrate a cross-sectional, side view of an X-ray source and an X-ray detector of the imaging system of FIG. 1 during an imaging process, according to an implementation of the disclosure.

FIG. 9F illustrates the example calibration system assembly of FIG. 9C in a leftward tilt state in accordance with embodiments of the technology disclosed herein.

FIG. 9G illustrates the example calibration system assembly of FIG. 9C in a rightward tilt state in accordance with embodiments of the technology disclosed herein.

Figure 1:
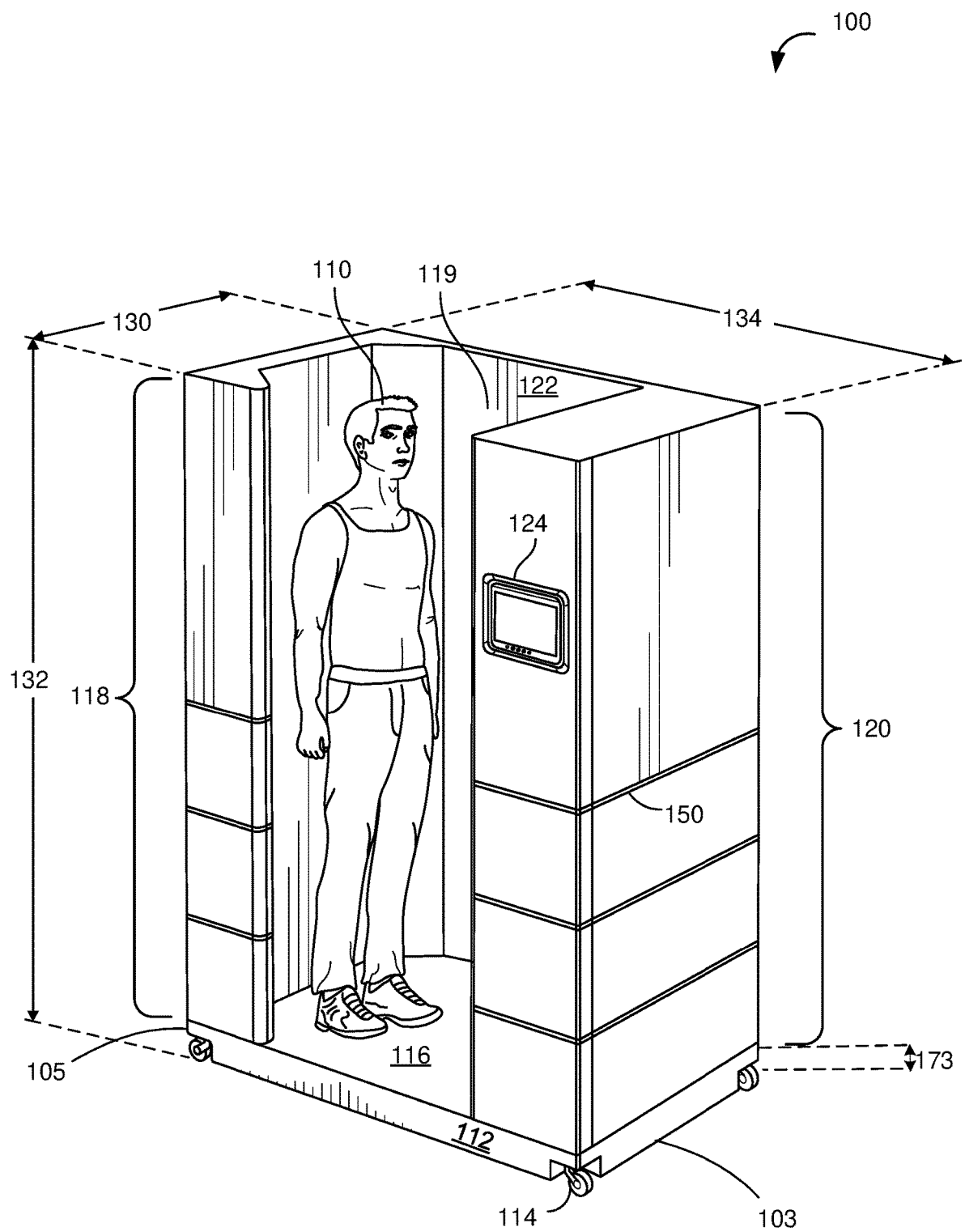
FIG. 1 illustrates an imaging system, according to an implementation of the disclosure.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Described herein are imaging systems for detecting objects that may be hidden under clothing, ingested, inserted, or otherwise concealed on or in a person's body. The details of some example embodiments of the systems and methods of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

As noted above, situations exist where objects hidden on or in a person's body, in or under clothing, etc. should be identified. Moreover, situations exist where the form factor of an imaging system is a consideration, e.g., when the imaging system must travel to a facility in which it is to be used, when the imaging system must be moved from one area (or room) to another through one or more doorways, etc. Accordingly, various embodiments of the present disclosure are directed to improvements to the form factor of an imaging system that leverages penetrating radiant energy transmitted by an X-ray source moved across a stationary object to an X-ray detector.

In particular, some embodiments may comprise an imaging system having a form factor that is smaller than conventional imaging systems, and that can be easily moved to and from different areas. For example, an imaging system configured in accordance with various embodiments may include appropriately-sized component parts that result in an overall form factor of the imaging system that allows the imaging system to be pushed/pulled through standard-sized doorway openings having limited height and width. Such appropriately-sized component parts may include a connecting member (described in greater detail below) that supports an X-ray source and an X-ray detector distally located from each other and allows for alignment of the X-ray source and X-ray detector. Moreover, various embodiments effectuate a particular range of movement of the connecting member (and the X-ray source and X-ray detector) that allows a subject to be scanned vertically within the form factor of the imaging system.

In some embodiments, during the imaging process, a lift mechanism may vertically translate the X-ray source and the X-ray detector joined by the connecting member across the object being imaged. For example, the lift mechanism may include linear actuators attached to cables threaded on pulleys and balanced by counterweight devices to effectuate the vertical translation of the X-ray source and the X-ray detector. In some embodiments, the lift mechanism may raise and lower the X-ray source and the X-ray detector at different rates which allows to angle or tilt the X-ray source relative to the X-ray detector and vice versa.

It should be understood that the systems and methods disclosed herein can be applied to existing imaging systems and methods. In other embodiments, an imaging system and method can be configured or designed (from the ground up) to operate in the disclosed manner. The imaging system comprising the X-ray source and the X-ray detector in accordance with various embodiments may be controlled by an imaging circuit implemented in or as part of the imaging systems' control unit. The imaging circuit can receive data from one or more sensors or derive data based on sensor data regarding movement and alignment of the X-ray source and the X-ray detector in order to decide whether or not to the X-ray source and the X-ray detector are aligned and/or moving in a synchronous fashion.

FIG. 1 depicts an example imaging system 100 configured in accordance with one embodiment. The imaging system 100 or components/features thereof may be implemented in combination with, or as an alternative to, other systems/features/components described herein, such as those described with reference to other embodiments and figures. The imaging system 100 may additionally be utilized in any of the methods for using such systems/components/features described herein. The imaging system 100 may also be used in various applications and/or permutations, which may or may not be noted in the illustrative embodiments described herein. For instance, imaging system 100 may include more or less features/components than those shown in FIG. 1, in some embodiments. Moreover, the imaging system 100 is not limited to the size, shape, number of components, etc. specifically shown in FIG. 1, although one or more aspects of imaging system 100 may have particular size/shape constraints in certain embodiments, as these one or more aspects may impact the overall form factor of imaging system 100.

A number of commercially available imaging systems use electromagnetic radiation to detect concealed objects and facilitate a body search process. Conventional imaging systems may be configured to utilize lower energy radiation during an imaging process. For example, lower energy imaging systems may use radiant energies, such as millimeter non-ionizing electromagnetic radiation and/or other lower energy radiation, such as backscatter X-ray radiation. During the imaging process, lower energy radiation may pass through outermost layers comprising an object, such as clothing, but is readily reflected off or scattered by any dense parts of the object. Accordingly, because lower energy imaging systems emit radiation that does not readily pass through the bulk of the object, they can only detect concealed threats hidden under the outermost layers only. For example, lower energy imaging systems can detect security threats concealed under a person's clothing, rather than those hidden in body cavities.

Other conventional imaging systems may be configured to utilize higher energy radiation. For example, higher energy radiation imaging systems may use radiant energies, such as X-ray radiation. While radiation levels used by higher energy systems may be lower than the radiation levels used in medical X-ray scanners, for example, the higher energy radiation is nonetheless transmitted through an object and is captured behind the object by a detector. For example, a continuous beam of X-ray radiation may be transmitted across an object being examined during an imaging process. A detector may capture the X-ray radiation and generate optical signals which are converted into electrical signals by a photodiode array within the detector. The electrical signals are then transmitted to a computing system that displays an image comprising the transmitted electrical signals and/or recorded via image recording equipment. By virtue of detecting radiant energy that is transmitted through the object rather than only measuring radiation that is reflected from the object, as the case may be with lower energy imaging systems, imaging systems using higher energy radiation (e.g., transmission X-ray radiation) can detect security threats concealed in a persons' body cavity, rather than those under a person's clothing.

Conventional imaging systems utilizing higher energy radiation may be configured in a number of ways. One such example of a conventional imaging system is an imaging system that comprises an X-ray source configured to emit a vertical beam of X-rays toward a vertically-oriented X-ray detector. During the imaging process, both the X-ray source the X-ray detector are configured to remain stationary while a subject is moved through the imaging system horizontally (e.g., by being placed on a conveyor belt). However, moving the subject through the imaging system not only necessitates a large imaging system, it also results in a number of operational problems (e.g., safety of a moving subject).

Another example of a conventional imaging system is one that comprises an X-ray source positioned at a midpoint level, relative to a stationary subject, and an X-ray detector positioned behind the stationary subject. During the imaging process, the X-ray source is configured to rotate about a horizontal axis while the X-ray detector is configured to move vertically. Because the X-ray source is not translated with the X-ray detector, but rather rotates, the X-ray beam emitted by the X-ray source enters the subject at an angle and thus traverses an excessively long path, especially when scanning lowermost and uppermost portions of the stationary subject. The excessively long path length traversed by the angled X-ray beam may prevent imaging of some essential body cavities (e.g., abdomen) and cause poor threat detection. Further, the long path length results in a number of motion synchronization issues between the X-ray source and the X-ray detector which also affect the quality of the images generated during the imaging process.

Yet another example of a conventional imaging system is one that comprises an X-ray source that is vertically translated with the X-ray detector in a synchronized fashion about a stationary object. Translating the X-ray source with the X-ray detector causes the X-ray beam to enter the subject horizontally, rather than at an angle, resulting in improved threat detection, as alluded to above, and improved image quality due to reduced geometric distortion. However, the conventional imaging systems that vertically translate the X-ray source with the X-ray detector are known to be heavy, bulky, and not easily transportable without extensive disassembly or mechanical lifting equipment.

An example imaging system having a form factor that is smaller than conventional imaging systems may be implemented as illustrated in FIG. 1. As shown in FIG. 1, the imaging system 100 comprises a frame encased within a housing mounted on a base assembly 112 which defines the width and length of the imaging system 100. The housing may house one or more imaging components configured to facilitate transmission X-ray imaging, one or more moving components configured to effectuate movement of the one or more imaging components, and/or other components. In some embodiments, the frame may comprise a metal scaffolding configured to provide structural support and/or framework for the imaging components and the movement components of the imaging system 100, as described in greater detail below.

In some embodiments, the base assembly 112 may include opposing first and second sides 103, 105. In some embodiments, the housing may comprise an X-ray source compartment 120 and X-ray detector compartment 118 mounted on the first and second sides 103, 105 of the base assembly 112, respectively. For example, the X-ray source compartment 120 may house an X-ray source and the X-ray detector compartment 118 may house an X-ray detector.

In some embodiments, the housing may comprise a connecting compartment 122 mounted between the first and second sides 103, 105 of the base assembly 112. For example, the connecting compartment 122 may be positioned between to the X-ray source compartment 120 and the X-ray detector compartment 118. In some embodiments, the connecting compartment 122 may house a connecting member configured to join the X-ray source housed in the X-ray source compartment 120 to the X-ray detector housed in the X-ray detector compartment 118, as described in detail below. In some embodiments, the connecting member may provide support, stabilize, and align the X-ray source with the X-ray detector during the imaging process.

In some embodiments, the X-ray source compartment 120, the X-ray detector compartment 118, and the connecting compartment 122 of the housing and the base assembly 112 of the imaging system 100 may each comprise an exterior and interior surface. The exterior and interior surfaces may be formed using the same or different material(s). For example, materials used to form the exterior surfaces of the X-ray source compartment 120, the X-ray detector compartment 118, the connecting compartment 122, and the base assembly 112 may include lead-lined steel, honeycomb aluminum, plastic and/or other such material configured to absorb X-ray radiation. By virtue of using the specified materials, the imaging system 100 may provide a physical shielding for scattered X-ray radiation emitted from an object during the imaging process (more commonly known as radiation scatter) to protect others in the immediate vicinity from radiation scatter is provided. In some embodiments, materials used to form the interior surfaces of the X-ray source compartment 120, the X-ray detector compartment 118, the connecting compartment 122, and the base assembly 112 may include structurally sound materials, such as a carbon-fiber composite, which are transparent to X-ray radiation.

In some embodiments, the housing of the imaging system 100 may be defined by at least three sides. Two sides may be formed by the X-ray source compartment 120 and X-ray detector compartment 118 mounted on the first and second sides 103, 105 of the base assembly 112, respectively, and a third side defined by the connecting compartment 122 mounted between the first and second sides 103, 105 of the base assembly. A fourth side may include an opening opposite the connecting compartment 122. The boundaries of the opening may be defined by the X-ray source compartment 120 and X-ray detector compartment 118 that extend towards the opening.

In some embodiments, the imaging system 100 may comprise an interior space 119, formed atop of the base assembly 112 and surrounded by the three ends of the housing, as alluded to earlier. The interior space 119 may be fully enclosed by the three sides and only partially enclosed by the fourth side to allow ingress/egress from the imaging system 100. For example, the interior space 119 may be fully enclosed on three sides by the X-ray source compartment 120, the X-ray detector compartment 118, and the connecting compartment 122. The fourth side partially enclosing the interior space 119 may comprise a side compartment (not shown), positioned opposite of the connecting compartment 122. In some embodiments, the side compartment may comprise a door (not shown) configured to enclose the interior space 119. For example, the door can be configured as a sliding door or a standard hinged door that opens and closes and provides access to the interior space 119 of the imaging system 100. In some embodiments, the door may be operably attached to the X-ray source compartment 120 and/or the X-ray detector compartment 118. In some embodiments, the door may be configured to slide between the X-ray source compartment 120 and the X-ray detector compartment 118.

In some embodiments, the interior space 119 may be fully and/or partially enclosed by a top cover (not shown) configured to enclose the interior space 119 from the top. In some embodiments, the top cover may be configured to be fully and/or partially removable. For example, the top cover may be removed to allow the imaging of an object which height may exceed the height 132 of the imaging system 100, as will be discussed in detail below.

In some embodiments, the interior space 119 may comprise a hollow cavity configured to receive a subject during the imaging process, as will be described in greater detail below. As used herein in some embodiments, the term "subject" may refer to an object that is being scanned by the imaging system 100, such as an inanimate object. As discussed in greater detail below, the object may also comprise a person, such as an inmate, a suspected criminal, a terrorist, or a person entering an area of high security (e.g., an airport).

In some embodiments, the base assembly 112 and the housing of the imaging system 100 mounted on top of the base assembly 112 may have reduced dimensions as compared to conventional imaging systems. For example, a width, height, and length of the one or more components may be sized so as to allow the imaging system 100 to pass through a standard-sized doorway (e.g., to accommodate a large person during an imaging process, or to ease the placement of an object onto the base assembly 112).

The dimensions of the imaging system 100 in this example include a width 130, a length 134, and a height 132. In some embodiments, the width 130 of the imaging system 100 may be approximately 84 cm, the length 134 may be approximately 182 cm, and the height 132 may be approximately 211 cm. In some embodiments, the base assembly 112 may include a height 173 which may contribute to of the height 132 of the imaging system 100. For example, the base assembly 112 may be approximately 10 cm high.

In some embodiments, the imaging system 100 may be configured to be transported. For instance, as shown in the embodiment of FIG. 1, the imaging system 100 may comprise at least four wheels or casters 114, mounted on the exterior surface of the base assembly 112. As imaging system 100 is moved, each of the casters 114 may roll, facilitating movement of imaging system 100. It should be understood that various embodiments contemplate the use of other mechanisms for moving imaging system 100, e.g., sliders, pads, and the like. For example, the imaging system 100 may be rolled through a doorway by engaging the casters 114.

In some embodiments, as alluded to above, the particular dimensions of the imaging system 100, such as the width and height 130, 132 may permit transportation of the imaging system 100 through standard doorways (or non-standard doorways having smaller dimensions). By virtue of the width and height 130, 132 of the imaging system 100 being less than a width and height of a standard-sized doorway, respectively, the imaging system 100 can fit through the standard-sized doorway of most commercial buildings. For example, a standard-sized doorway in a commercial building may be approximately 86 cm wide and approximately 213 cm high. Accordingly, because the width 130 and height 132 of the imaging system 100 is approximately less than 84 cm and less than 211 cm, respectively, the particular dimensions of the imaging system 100 permit the imaging system 100 to be transported through the standard-sized commercial doorway.

Furthermore, while the imaging system 100 may be configured to be transported through standard-sized doorways of most commercial buildings, the particular dimensions of the imaging system 100 may also accommodate a person of larger than average dimensions during the imaging process. For instance, a large person may have a width and height of approximately 80 cm and 200 cm, respectively. Accordingly, the dimensions of the imaging system 100 of the embodiment illustrated in FIG. 1 exceed the dimensions of the large person to accommodate the imaging process. For example, the dimensions of the imaging system 100 may exceed the dimensions of a large person by ten percent. Notably, while the imaging system 100 is large enough to accommodate the imaging of a large person it still has a form factor smaller than the conventional imaging systems. For example, conventional imaging systems are often dimensioned to substantially exceed the width and height of the person being scanned. Accordingly, by virtue of greatly surpassing the dimensions of the person being scanned, conventional imaging system may have to be transported in modules and reassembled upon arrival.

As alluded to above, various embodiments of imaging system 100 may have a form factor that allows the imaging system 100 to be transported within some establishments (e.g., government facilities) having doorways with reduced dimensions compared to other commercial, standard-sized doorways. For example, prison doorways may have height of approximately 200 cm. In some embodiments, the imaging system 100 may have dimensions so as to permit transportation through doorways that are approximately 200 cm high. For example, the height 132 of the imaging system 100 may be less than 200 cm. As described in greater detail below, the imaging system may comprise a lift mechanism that may temporarily extend the height 132 of the imaging system 100 during the imaging process in order to accommodate a person whose height exceeds 200 cm.

In some embodiments, the one or more exterior surfaces of the housing of the imaging system 100 may comprise one or more markings and/or decorative features 150. For instance, in some embodiments, the exterior surface of the X-ray component 120 may comprise markings indicating the radiographic features (e.g., the strength of the X-ray) associated with the imaging system 100. In some embodiments, the one or more exterior surfaces of the imaging system 100 may comprise an identification (e.g., a name) of the facility that is utilizing the imaging system 100. In some embodiments, the one or more exterior surfaces of the housing of the imaging system 100 may comprise one or more decorative features such as decorative feature 150 used to enhance cosmetic appearance of imaging system 100. In some embodiments, the one or more exterior surfaces of the housing of the imaging system 100 may comprise any or all of the foregoing markings, decorative features, or other relevant elements as would become apparent to one skilled in the art upon reading the present application.

Imaging Process

In some embodiments, an object being imaged by the imaging system 100 may be placed between the X-ray source compartment 120 and the X-ray detector compartment 118. For example, as shown in the embodiment of FIG. 1, the object being examined is a person 110 who enters the interior space 119 of the imaging system 100 by stepping onto a floor 116 affixed to the interior surface of the base assembly 112. Alternatively, a person using a walker, crutches, or a wheelchair may also be placed onto the floor 116 by utilizing a ramp or other such components configured to facilitate such placement.

As alluded to above, in some embodiments, the person 110 may access the interior space 119 of the imaging system 100 by entering through the opening in the housing defined by the X-ray source compartment 118 and the X-ray detector compartment 120. As alluded to above, in some embodiments, the person 110 may access the interior space 119 of the imaging system 100 by opening and/or sliding the door configured to fully and/or partially enclose the interior space 119. Upon entering the interior space 119, the person may be positioned to face the X-ray source compartment 118. In some embodiments, the person can be positioned to face the X-ray detector compartment 120. Once the person 110 is properly positioned, the door may be closed, and the imaging process may be initialized. In some embodiments, during the operation of the imaging system 100, the person 110 may be instructed to stand motionless.

In some embodiments, as alluded to above, the small form factor of the imaging system 100 may prevent and/or alleviate difficulties associated with accessing the interior space 119. That is, the particular dimensions of the base assembly 112, such as the height 173, may minimize the distance relative to the floor on which the imaging system 100 may be placed. For example, the person 110 may need to step on and off the floor 116 of the base assembly 112 during the imaging process. By virtue of the reduced height 173 of the base assembly 112, as compared to conventional imaging systems, the person may need to overcome a relatively short distance.

In some embodiments, the duration of the imaging process may range from approximately 0.5 to 5 seconds. Conventional imaging systems typically perform the imaging process in approximately 8 to 10 seconds. Upon completing the imaging process, and as discussed in greater detail below, the image may be generated and transmitted to be examined for concealed threats. In some embodiments, the door may be opened, and the person may exit the imaging system 100 by stepping off the floor 116 of the base assembly 112 thereby completing the imaging process.

In some embodiments, the imaging system 100 may be operated by an operator by entering one or more user commands via a control interface. For example, the operator may initiate an imaging process by entering an appropriate command via the control interface of a the control panel 124 or other associated control interface.

In some embodiments, the imaging system 100 may be configured to be operated from a remote location. For example, the operator may initiate the imaging process by entering an appropriate command via a control interface within a computing platform (not shown) communicatively coupled to the imaging system 100 located in a different physical location than the computing platform. The operator may both initiate the imaging process and view one or more images generated by the imaging system 100 from the computing platform.

In some embodiments, the imaging system 100 may be operated automatically. For example, upon detecting that an object has been placed onto the floor 116 of the base assembly 112, the imaging process may be initiated. The images generated during the automatic imaging process may be transmitted to the computing platform.

X-Ray Assembly

Figure 2A:
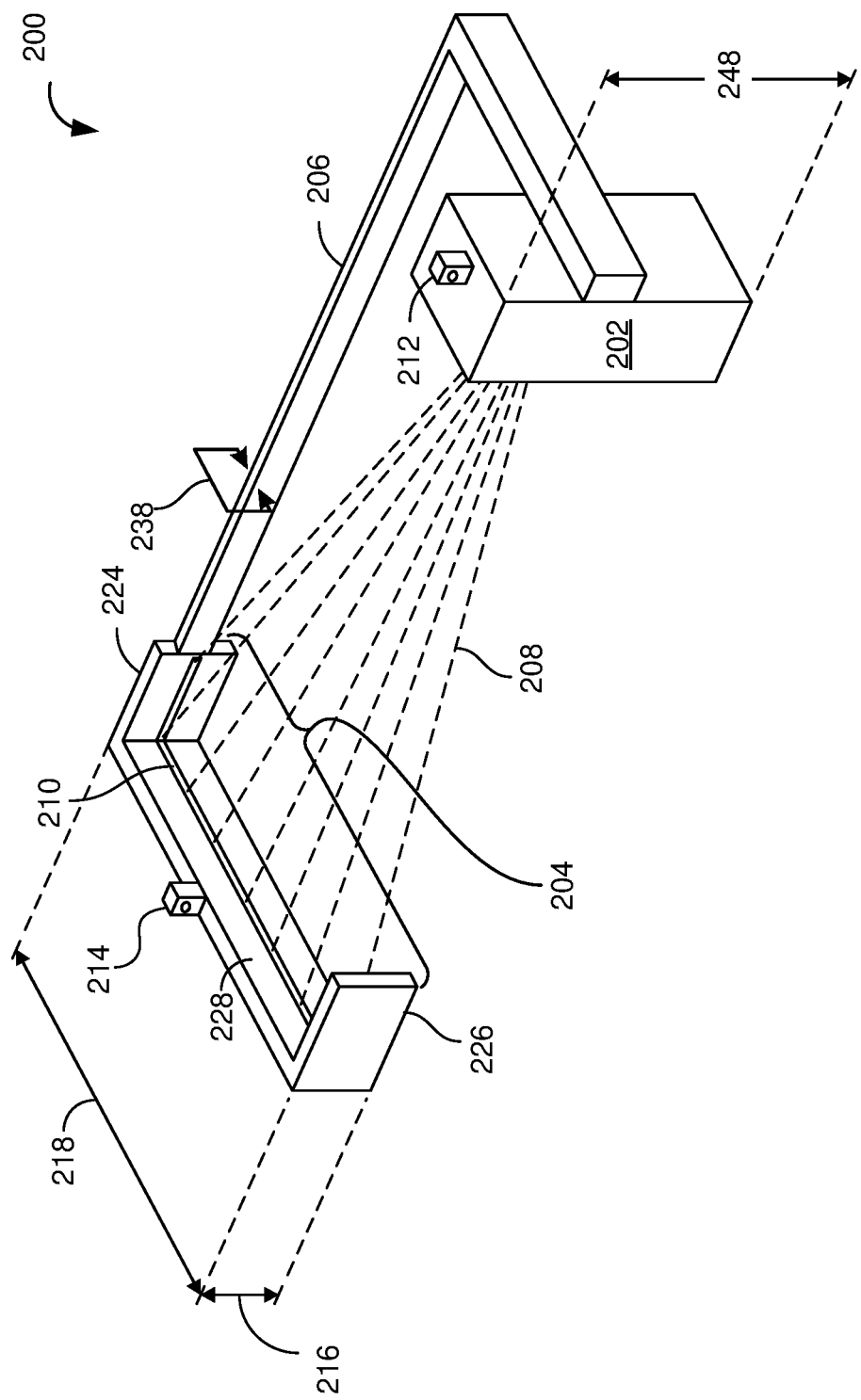
FIG. 2A illustrates an X-ray assembly of the imaging system of FIG. 1, according to an implementation of the disclosure.

FIG. 2A illustrates an example X-ray assembly 200 of the imaging system 100. The X-ray assembly 200 comprises an X-ray source 202, an X-ray detector 204, and a connecting member 206. As alluded to earlier, and as illustrated in FIG. 1, the X-ray source 202 may be housed within the X-ray source compartment 120. The X-ray detector 204 may be housed within the X-ray detector compartment 118, and the connecting member 206 may be housed within the connecting compartment 122.

X-Ray Source

As noted previously, the X-ray source 202 may be configured to emit a continuous beam of higher energy X-ray radiation captured by the X-ray detector 204 to facilitate detection of concealed objects (e.g., in body cavities). For instance, as illustrated in FIG. 2A, X-ray source 202 may comprise an X-ray generator (e.g., Monoblock® generator) capable of producing a beam of X-rays with a maximum energy of at least 120-180 keV and a maximum tube current of at least 0.1-10 milliamperes. In some embodiments the X-ray source 202 may have a height 248. For instance, and as illustrated in FIG. 2A, the height 248 of the X-ray source 202 may be approximately 40 cm.

During the imaging process, the X-ray source 202 is translated vertically across the object being imaged. Because the emitted X-ray radiation must be captured by the X-ray detector 204, the X-ray source 202 and the X-ray detector 204 must be aligned during the translational movement. Maintaining alignment may require stabilizing the X-ray source 202 and the X-ray detector 204 to maintain substantially the same relative position of these two components during the imaging process.

Figure 2B:
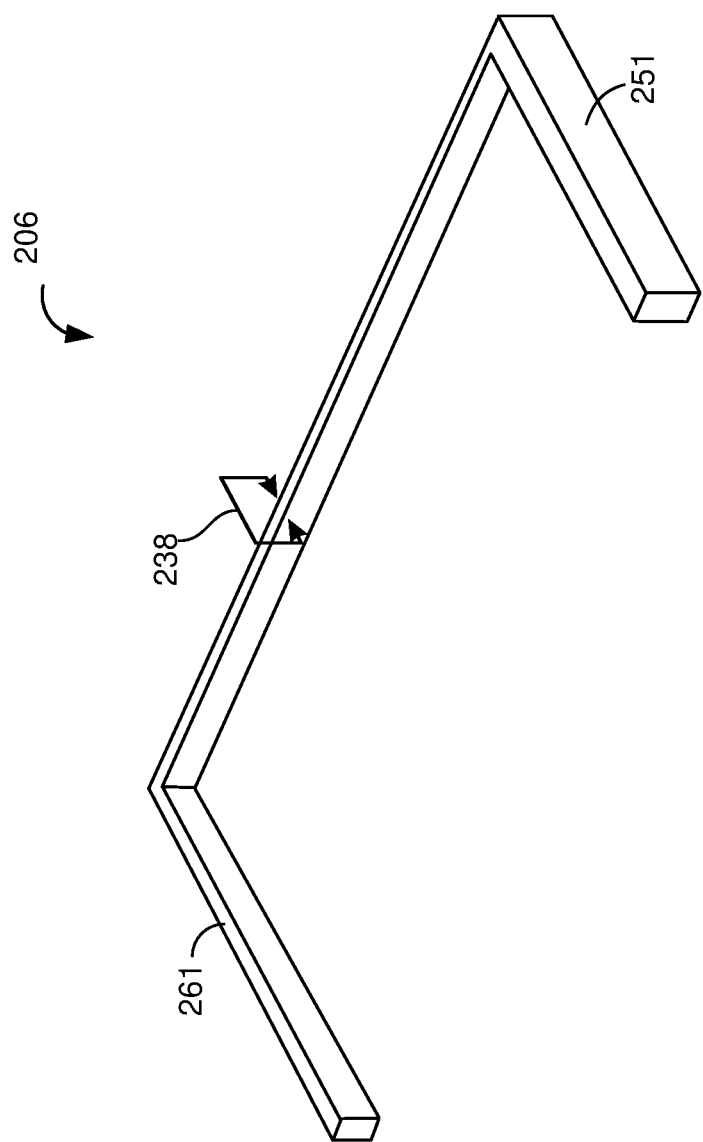
FIG. 2B illustrates a connecting member of the imaging system of FIG. 1, according to an implementation of the disclosure.

In some embodiments, X-ray source 202 may be mounted onto the connecting member 206 to assist with maintaining substantially the same position of the X-ray source 202 relative to the X-ray detector 204 and aligning the X-ray source 202 with the X-ray detector 204 during the imaging process. For example, as illustrated in FIG. 2B, the X-ray source 202 may be mounted on a first arm 251 of the connecting member 206. The first arm 251 of the connecting member 206 may be distally located from a second arm 261 of the connecting member 206.

In some embodiments, a filter wheel containing one or more filters may be placed in close proximity (within a few centimeters) to the output of the X-ray source 202 so as to intercept and filter the X-ray beam generated by the X-ray source 202. For example, the one or more filters may be formed of aluminum and copper of varying thicknesses (e.g., Al 1-10 mm, Cu 0.1-1 mm).

Collimator

In some embodiments, the imaging system 100 may comprise at least one collimator (e.g., collimator 213 illustrated in FIG. 3A) to control the spatial extent of a stream of X-ray photons emitted from a focal spot of the X-ray source. By limiting the spatial extent of the X-ray beam (e.g., by confining the beam of X-rays to a particular area) the image quality may be improved and the radiation dose reduced. A single-slit collimator that shapes the X-ray beam to a thin sheet or "fan-beam", is one such example of a collimator. Another example is a multi-slit collimator having a number of openings or through holes formed side by side, each for guiding and passing the X-ray radiation. Typically, a collimator is fabricated using a high-density metal and/or a refractory metal capable of absorbing, rather than passing the radiation through, such as tungsten or lead. For example, the collimator may be configured to have an approximately 0.25 mm slit through which the X-ray radiation passes.

In some embodiments, the collimator may be configured to remain in a fixed position relative to the X-ray source 202. In some embodiments, the collimator may be configured to move about the X-ray source 202. In yet other embodiments, a plurality of collimators may be used. For example, a first collimator may be a fixed-slit collimator while a second collimator may be a rotating collimator.

In some embodiments, the collimator may be placed adjacent the X-ray source 202 to intercept and collimate the beam of X-rays into a fan-beam of X-rays 208 corresponding to the dimensions of the X-ray detector 204. By virtue of collimating the beam of X-rays, the beam of X-rays may be confined to an area having particular width and height. For example, the collimated fan-beam of X-rays 208 is confined to an area approximately 30 cm wide and approximately 2 mm high at the X-ray detector 204 side, while being approximately 0.25 mm high as it is emitted from the X-ray source 202. Accordingly, although the beam of X-rays expands in both vertical and horizontal directions as it propagates, by using the collimator, as alluded to above, X-ray radiation is confined to an active area 210 of the X-ray detector 204, described in detail below. Accordingly, the collimator allows to confine the X-rays to be intercepted by the X-ray detector 204 having a narrow active area which in turn results in a decreased size of the X-ray detector 204 and contributes to the form factor of the imaging system 100, as described below.

X-Ray Detector

As alluded to above, the X-ray detector 204 may be configured to capture the beam of X-ray radiation emitted from the X-ray source 202 and generate optical signals which are converted into electrical signals by a photodiode array included in the X-ray detector 204. During the imaging process, the X-ray detector 204 is translated vertically in alignment with the X-ray source 202.

In some embodiments, particular dimensions of the X-ray detector 204 may not only contribute to maintaining alignment between the X-ray detector 204 and the X-ray source 202 and/or stabilizing the X-ray detector 204 during the imaging process, but also to the overall form factor of the imaging system 100.

Reduced size and weight of the X-ray detector 204, as compared to X-ray detectors used in conventional imaging systems, is one example which can result in greater stability during the vertical translational movement alluded to earlier. This is because the connecting member 206 onto which the X-ray detector 204 is mounted may be susceptible to vibrational and/or other mechanical forces during the vertical translational movement. These mechanical forces acting upon the connecting member 206 may result in misalignment between the X-ray detector 204 and the X-ray source 202 and cause poor image quality. Conventional imaging systems that do not consider the form factor focus on stabilizing the X-ray detector (i.e., reducing the mechanical forces acting upon the connecting member which bears the X-ray detector) by increasing the size of the connecting member. However, this may result in an increased weight and size of the imaging system itself. For example, conventional imaging systems typically weigh approximately 900 kg and has dimensions of approximately 2.4 m wide, 2.4 m long, and 2.4 m high. Of particular concern is the inability to transport such large imaging systems without extensive disassembly and/or without using mechanical lifting equipment.

In some embodiments, the X-ray detector 204 may have a height 216 and width 218. For instance, and as illustrated in FIG. 2A, the height and width 216, 218 of the X-ray detector 204 may be approximately 10 cm and 80 cm, respectively. In some embodiments, the width 218 of the X-ray detector 204 may approximately correspond to the width 130 of the imaging system 100 illustrated in FIG. 1.

In some embodiments, the X-ray detector 204 may comprise at least one detector array, an example of which can be a photodiode array. In some embodiments, a detector array may comprise one or more photodiode arrays. In some embodiments, the photodiode array may be a linear array. For instance, as illustrated in FIG. 2A, the X-ray detector 204 may comprise a detector array comprising at least one array of photodiodes. In some embodiments, the at least one photodiode array of the X-ray detector 204 may comprise a plurality of individual photodiodes. For example, the at least one photodiode array of the X-ray detector 204 may comprise 640 photodiodes.

In some embodiments, each of the photodiodes within the photodiode array may have an attached scintillation material (e.g., cadmium tungstate or cesium iodide) and have particular dimensions. For example, individual photodiodes within the one or more photodiode array of the X-ray detector 204 may be approximately 1.6 mm high and approximately 1.6 mm wide. In some embodiments, the X-ray detector 204 may comprise approximately 40 photodiode arrays, each containing 16 photodiodes, for a total of 640 photodiodes. In some embodiments, all of the photodiode arrays of the X-ray detector 204 may each be approximately 71 cm long.

In some embodiments, the collimated fan-beam of X-rays 208 may pass through an aperture that confines the dimension and movement of the X-ray beams 208 to the X-ray detector 204. In some embodiments, the collimated fan-beam of X-rays 208 may be confined to a particular area within the X-ray detector 204. For example, the collimated fan-beam of X-rays 208 may be confined to an active area 210 of the X-ray detector 204. The active area 210 of the X-ray detector 204 may be defined by the photodiode array. For example, the X-ray source 202 may generate a collimated single beam of X-rays which may only require a narrow active area 210. A narrow active area 210 may in turn result in the X-ray detector 204 having reduced dimensions and/or weight. As alluded to above, reducing the size and/or weight of the X-ray detector 204 results in maintaining the form factor of the imaging system 100.

Photodiode Array

In some embodiments, the at least one photodiode array of the X-ray detector 204 may be illuminated by the fan beam of X-rays 208 generated by the X-ray source 202. In some embodiments, the photodiodes and accompanying scintillators, within the photodiode array may absorb radiant energy generated by the X-ray source 202. Upon absorbing a level of radiant energy, the photodiodes may generate an electrical signal. In some embodiments, the electrical signal generated by the photodiodes may result in an output data transmitted via analog and/or digital electronic circuits. The output data may comprise image data being communicated to a computing platform for image display.

In some embodiments, linescan geometry may be utilized to read all the photodiodes within each of the one or more photodiode array of the X-ray detector 204. In some embodiments, image data may be processed by imaging processing software or a program configured to generate a digital image of the scanned object.

In some embodiments, a readout speed (i.e., the speed at which individual photodiodes with the photodiode array are processed) of the photodiode arrays may be determined by a microprocessor controller. For example, all of the 640 photodiodes within the 40 photodiode arrays within the X-ray detector 204 may be read out in approximately 3 milliseconds. The readout speed may determine the imaging process time. For example, as alluded to above, the photodiode arrays within the X-ray detector 204 may be read out in approximately 3 milliseconds. Because the imaging system 100 is configured to read out 1333 "scan lines" during the imaging process, if follows that the total scan time will be approximately 4 seconds long. Individual scan lines may correspond to a resolution of the resulting image generated during the imaging process.

Accordingly, the X-ray detector 204 must complete the readout of all 640 photodiodes before reading out the next scan line. That is, the read-out speed of 3 milliseconds for all the photodiodes within the X-ray detector 204 can be completed before the next vertical displacement. This can be achieved by ensuring the height of the scan line is approximately the same as the height of the photodiode array. For example, given an average height of a person is approximately 200 cm, each scan line is approximately of 1.6 mm high which corresponds to the height of the photodiode array (i.e., approximately 1.6 mm).

In some embodiments, X-ray detector 204 may comprise an X-ray detector assembly including a back member, a first member 226, and a second member 224, such that the first and second members 226, 224, are coupled to each side of the back member 228. Alternatively, the first and second members 224, 226, and back member 228 may be a single unit/formed as a single unit. The X-ray detector assembly may have a height 216 and a width 218. For instance, and as illustrated in FIG. 2A, the height and width 216, 218 of the X-ray detector assembly may be approximately 10 cm and 80 cm, respectively.

In some embodiments, the first and second members 226, 224 of the X-ray detector assembly may be coupled to either side of back member 228 at a right angle. Accordingly, the X-ray detector 204 comprising the X-ray detector assembly, defined by the back member 228 and the first and second members 226, 224, may be "U-shaped". In some embodiments, the first and second members 226, 224 may be attached to either side of back member 228 at an obtuse angle. By virtue of using the X-ray detector assembly comprising the first and second members 226, 224, attached to either side of the back member 228, the X-ray detector may be configured to house the at least one photodiode array having the same and/or greater length than the width 218 of the X-ray detector assembly.

For instance, and as illustrated in FIG. 2A, the photodiode array may be dimensioned to be as long as an average width of a person (e.g., approximately 76 cm), while still fitting within the dimensions of the width 218, which may be smaller than the average width of the person. That is, the at least one photodiode array housed in the first and second members 226, 224 of the X-ray detector assembly can detect the X-rays emitted by the X-ray source 202 by virtue of being "wrapped" around at least one portion of the subject's body. By housing the at least one photodiode array within the U-shaped X-ray detector 204, as alluded to above, the X-ray detector assembly can be approximately only ten percent smaller than the imaging system 100. That is, due to the U-shape of the X-ray detector 204, the entirety or requisite portion of the fan-shaped X-ray beam 208 needed for complete imaging of a subject is captured, despite the vertical and horizontal expansion of the X-ray beam. This, in conjunction with use of the aforementioned collimator (which confines the X-ray radiation to an active area 210 of the X-ray detector 204) results in improved X-ray detection within the small form factor of the imaging system 100.

For example, during the imaging process, the person 110 may stand facing the X-ray source 202 while the person's 110 back may be turned to the X-ray detector 204, or vice versa (e.g., facing the X-ray detector 204). Accordingly, one-half of the subject's frontal plane may be covered or encompassed by X-ray detector 204 (e.g., by the first and second members 226, 224 and the back member 228) by virtue of the X-ray detector 204 having the U-shape, as alluded to earlier. That is, the at least one photodiode array housed in the U-shaped X-ray detector 204 may capture emitted radiation by covering or encompassing almost the entire subject despite the fact that the back member 228 is shorter than the width of the subject being imaged. Further, by virtue of housing the photodiode array 210 within the first and second members 226, 224, rather than housing the photodiode array 210 only within the back member 228 the small form factor of the imaging system 100 illustrated in FIG. 1 may be achieved.

In some embodiments, the X-ray detector 204 need not be linear in shape, but rather can be angled so as to conform to the shape of the base assembly 112 of the imaging system 100. By virtue of the X-ray detector 204 conforming to the shape of the base assembly 112, rather than being linear, allows the base assembly to have a reduced size, which contributes to the small form factor of the imaging system 100. In particular, and referring back to FIG. 2A, it can be appreciated that members 226, 224 of X-ray detector assembly are configured to be substantially perpendicular to the back member 228. However, in other embodiments, side members 226, 224 may be angled relative to the back member 228. For example, and referring now to FIG. 3B, side members 224, 226 may be angled to conform to the angled cutouts in which side members 224, 226 may rest when not performing an imaging process.

Safety Monitoring System

In some embodiments, the imaging system 100 may comprise one or more radiation shielding components. The radiation shielding components may be formed from a radiation absorbent material such as lead, tungsten, and/or other such material capable of absorbing radiant energy emitted by the X-ray source during the imaging process. For example, and as illustrated in FIG. 2A, the X-ray detector 204 may comprise one or more radiation shielding components at each first and second member of the X-ray detector 204. During the imaging process, the X-ray source 202 is directed at the X-ray detector 204 and one or more radiation shielding components at each of end of the X-ray detector 204. Because the collimator limits the horizontal width of the fan-beam of X-rays 208 emitted by the X-ray source 202 to slightly less that the width of the X-ray detector 204, the occurrence of non-illuminated photodiodes at each end of the X-ray detector 204 may indicate that the fan-beam of X-rays 208 is properly aligned with the X-ray detector 204 in a horizontal direction. That is, this provides a way to ensure that the sides (or requisite portions) of the fan-beam of X-ray 208 are being intercepted and thereby blocked by the one or more radiation shielding components at each of the end of the X-ray detector 204.

Connecting Member

As noted previously, alignment between the X-ray source and the X-ray detector is maintained during the imaging process in order to obtain an accurate image. Conventional imaging systems often maintain alignment between an X-ray source and an X-ray detector source by virtue of one of more components supporting the X-ray source and the X-ray detector. However, these components are often heavy and large resulting in bulky imaging systems that cannot be transported easily.

As alluded to above, in some embodiments, the connecting member 206 may rigidly join the X-ray source 202 to the X-ray detector 204. In some embodiments, connecting member 226 may be formed from a substantially rigid material, such as steel or any other such material capable of maintaining a rigid shape.

As illustrated in FIG. 2B, the connecting member 226 may be "C-shaped". For example, and as alluded to earlier, the X-ray source 202 may be mounted on the first arm 251 of the connecting member 206 while the X-ray detector 204 may be mounted on the second arm 261, opposite the first arm 251 of the connecting member 226. Conventionally, a connecting member, similar to connecting member 206 illustrated in FIG. 2B, may be appropriately sized in order to maintain substantially the same position of the X-ray detector and X-ray source during the imaging process and facilitate alignment between the X-ray source and X-ray detector. As alluded to earlier, because the collimated fan-beam of X-rays 208 emitted by the X-ray source 202 is focused to a particular area the X-ray detector 204 (e.g., the active area 210), the X-ray detector 204 need only be as narrow as the width and length of the fan-beam of X-rays 208 (i.e., substantially smaller than the X-ray detector used in conventional imaging systems). By reducing the size of the X-ray detector 204, as contemplated in accordance with various embodiments, the connecting member can be configured to be lighter and have a form factor that is smaller than a conventional connecting member, which contributes to the form factor of the imaging system 100. For example, the connecting member 206 may comprise a width 238, which may be approximately 1.9 to 10 cm. In some embodiments, the width 238 of the connecting member 206 may comprise the same width as the width of the second member 224 of the X-ray detector assembly, illustrated in FIG. 2A, as discussed above. That is, the width 238 of the connecting member 206 may be such that it would not increase the width 130 of the imaging system 100 illustrated in FIG. 1.

In some embodiments, during the imaging process the connecting member 226 is configured to maintain alignment between the X-ray source 202 and the X-ray detector 204. For example, as the X-ray source 202 and the X-ray detector 204 are raised and lowered, the alignment between the X-ray source 202 and X-ray detector is maintained by virtue of the rigid connection provided by the connecting member 226. In some embodiments, using the connecting member 226 to maintain alignment between the X-ray source 202 and X-ray detector 204 during the imaging process, rather than relying on feedback sensors, for example, results in alignment with a lower margin of error (e.g., a margin of error up to 0.13 mm) compared to conventional imaging systems. In some embodiments, maintaining rigid alignment between the X-ray source 202 and X-ray detector 204 reduces a risk of disruptions (e.g., distortions in the acquired image) during the imaging process.

Attachment Points

As alluded to earlier, during the imaging process, the X-ray assembly 200 of the imaging system 100 is translated vertically. Often, conventional imaging systems raise and lower an X-ray assembly within an imaging system frame by utilizing a lift mechanism which attaches to the X-ray assembly via a single attachment point (and thus uses a single actuator). However, the single attachment point often causes the X-ray assembly to unintentionally twist causing misalignment between the X-ray source and the X-ray detector resulting in undesirable image distortions. As alluded to above, to compensate for these unintentional motions, conventional imaging systems focus on increasing the size of the connecting member resulting in bulky and large imaging systems to achieve a desired amount of stability in the X-ray assembly. For example, conventional imaging systems tend to rely on connecting members that have larger dimensions, are heavier, and are more difficult to move and actuate.

In contrast, in some embodiments, the X-ray assembly 200 is raised and lowered by a lift mechanism which attaches to the X-ray assembly via at least two individual attachment points. For example, and as illustrated in FIG. 2A, a first attachment point 214 may be mounted on the X-ray detector 204, and a second attachment point 212 may be mounted on the X-ray source 202. The first and second attachment points 212, 214, may be coupled to a first and second linear actuators, respectively, as described below.

The first and second attachment points 214, 212 may be positioned at opposite ends of the X-ray assembly 200, i.e., at or near a center of mass of each of the X-ray detector 204 and the X-ray source 202, respectively. This configuration may reduce any potential mechanical forces (e.g., stress forces) that the connecting member 206 must overcome during the vertical translation movement. Accordingly, reducing any potential stress forces which the connecting member 206 must overcome during the vertical translation movement, allows the connecting member 206 to have a narrow width 238 while still providing stability and alignment during the imaging process, as described above. Further, a reduction in size of the connecting member 206 allows the form factor of the imaging system 100 illustrated in FIG. 1 to be maintained.

In yet other embodiments, using at least two attachment points results in actuating the X-ray detector 204 independently or at a different rate than the X-ray source 202, as described further below.

Lift Mechanism

Figures 3A, 3B:
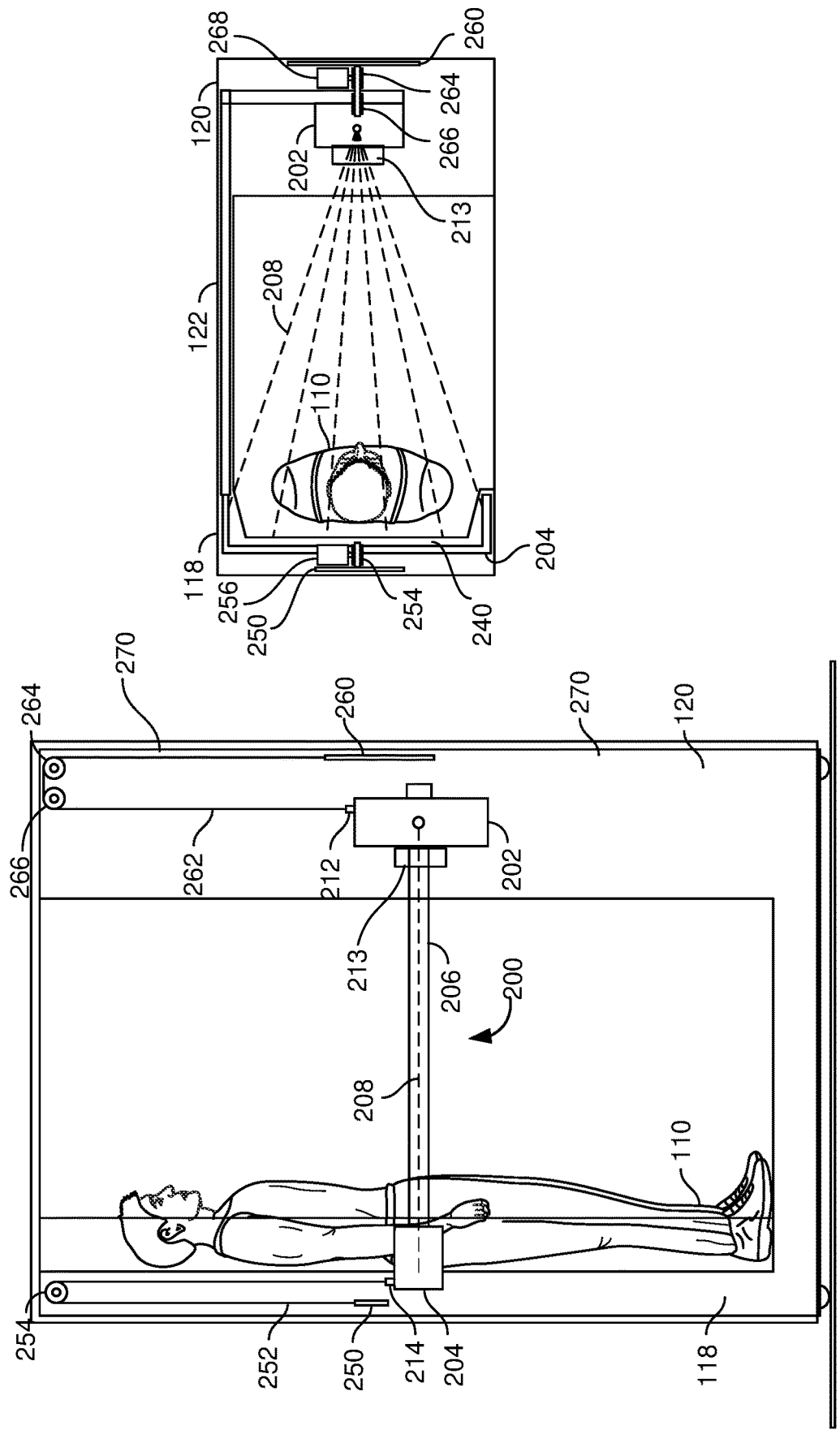
FIGS. 3A-3B illustrate a cross-sectional, side view and a cross-sectional, top down view, respectively of the imaging system of FIG. 1, according to an implementation of the disclosure.

An example imaging system having a form factor that is smaller than conventional imaging systems in which an X-ray assembly is translated vertically may be implemented as illustrated in FIGS. 3A-3B. FIG. 3A provides a cross-sectional, side view of the imaging system 100. FIG. 3B provides a cross-sectional, top down view of the imaging system 100.

In some embodiments, the imaging system 100 comprises a lift mechanism comprising one or more motors, one or more linear actuator devices, one or more pulleys, one or more cables, one or more counterweight devices, and/or other components configured to lower and raise the X-ray assembly 200 within a frame of the imaging system 100.

For example, the lift mechanism comprises the electric motors 256, 268 illustrated in FIG. 3B, as a source of motive power. The motors 256, 268 may be connected to an external power source (e.g., a wall outlet or a power storage device), and an inverter. The power storage device can include, for example, one or more batteries, capacitive storage units, or other storage reservoirs suitable for storing electrical energy that can be used to power one or more motors. When power storage device is implemented using one or more batteries, the batteries can include, for example, nickel metal hydride batteries, lithium ion batteries, lead acid batteries, nickel cadmium batteries, lithium ion polymer batteries, and other types of batteries.

In some embodiments, the motors 256, 268 may be controlled by a microprocessor controller. The microprocessor controller may receive data from one or more encoders mounted on the X-ray source 202 and the X-ray detector 204, respectively. The one or more encoders may transmit data to the microprocessor controller related to the position and speed of the X-ray source 202 and the X-ray detector 204, respectively. In some embodiments, microprocessor controller may be configured to align the X-ray detector 204 with the X-ray source 202 prior to the imaging process, as described below.

In some embodiments, the motive power generated by the motors 256, 268 in communication with the one or more linear actuator devices may be transmitted to cables 252, 262 threaded on pulleys 254, 264, 266, respectively for actuating movement of the X-ray assembly 200. For example, the cables 252, 262 may comprise belts and/or and flexible straps. In some embodiments, the cables 252, 262 may comprise a cross section that is approximately 1.27 by 0.32 cm. In some embodiments, a longitudinal surface of the cables 252, 262 may comprise one or more groves configured to engage corresponding teeth on the one or more corresponding pulleys (e.g., the pulleys, 254, 264, 266).

In some embodiments, the pulleys 254, 266, and 266 may comprise a toothed pulley, an idler pulley, and/or any such pulley configured to accommodate the translational movement of the cables 252, 262. In some embodiments, the pulleys 254, 264, 266 may comprise a pulley member wherein rotation of the pulley member is provided about a substantially horizontal axis, at least in one position of use.

In some embodiments, the linear actuator devices communicatively coupled to the motors 256, 268 may comprise a lift cylinder and a piston. One example of the lift cylinder is a hydraulic device configured for applying a required force. In come embodiments, the linear actuator devices comprise at least one of a hydraulic cylinder, a servo-motor, a geared system, and a rack and pinion system. In some embodiments, the lift cylinder of the linear actuator devices may be in communication with the piston, which may have a moveable actuator arm. The motors 256, 268 may generate and communicate a force to the lift cylinders driving the actuator arm linearly.

In some embodiments, the lift mechanism is configured to lower and raise the X-ray assembly 200 within a frame 270. The frame 270 may comprise one or more vertical guides and/or channels. The one or more vertical guides or channels may be configured to provide a vertical path through which the X-ray assembly 200 moves as it is being raised and lowered. For example, the X-ray source 202 and the X-ray detector 204 may move within vertical paths of the frame 270 as the X-ray assembly 200 is raised and lowered. In some embodiments, the vertical paths of the frame 270 through which the X-ray source 202 and the X-ray detector 204 move may not have same dimensions. For example, the X-ray source 202 may move within the vertical path having a first height range, whereas the X-ray detector 204 may move with the X-ray source 202 but within the vertical path having a second height range that exceeds the first height range, as described in detail below.

As alluded to earlier, the cables 252, 262 supporting the X-ray assembly 200 during the imaging process may be attached to the individual attachment points 214, 212 mounted on the X-ray detector 204 and the X-ray source, respectively. For example, cable 252 comprises a first terminus at the attachment point 214 mounted on the X-ray detector device 204, while cable 262 comprises a first terminus at the attachment point 212 mounted on the X-ray source 202. The cables 252, 260 may be secured at the attachment points 214, 212 by any number of known fasteners. For example, the one or more cables 252, 260 may be secured by standard rigging hardware feature such as an eye splice provided in a steel cable and sometimes referred to as a "molly hogan" or "dutch" eye. Such a feature may be wrapped around a protrusion on a device to be lifted (e.g., the X-ray detector 204 and the X-ray source 202), thereby providing for force-transmitting communication between the two components.

In some embodiments, the lift mechanism comprises one or more counterweight devices to facilitate the movement of the X-ray assembly 200 by providing a counter-balancing mechanism that allows the X-ray assembly 200 to move efficiently and easily within the frame 270. For example, cable 252 may be threaded through the pulley 254 and extend downwardly to interconnect with a counterweight device 250. Similarly, the cable 262 may be threaded through pulleys 266, 264, respectively, and extend downwardly to interconnect with a counterweight device 260.

In some embodiments, the counterweight devices 250, 260 may be constructed from a plate of iron or other heavy metal. For example, the counterweight device 250 may be approximately 30 cm long, 30 cm wide, and 1.9 cm deep, and have a weight approximately corresponding to the weight of the X-ray source 202 (e.g., 22 kg). Similarly, the counterweight device 260 may be approximately 10 cm long, 30 cm wide, and 0.75 cm deep, and have a weight approximately corresponding to the weight of the X-ray detector 204 (e.g., 7.2 kg).

In some embodiments, as alluded to earlier, the lift mechanism is configured to raise and lower the X-ray assembly 200 by energizing the motors 256, 268 which power the linear actuator devices that actuate and translate the movement of the cables 252, 262 threated onto pulleys 254 and 264, 266, respectively, to vertically translate the X-ray detector 204 and the X-ray source 202. The weight of each of the X-ray detector 204 and the X-ray source 202 being lifted may apply a force to corresponding pulleys 254 and 264, 266 via the corresponding cables 252, 262, respectively. The force applied via the cables 252, 262 may be countered by the counterweight devices 250, 260 interconnected with the cables 252, 262, respectively.

Figure 4A:
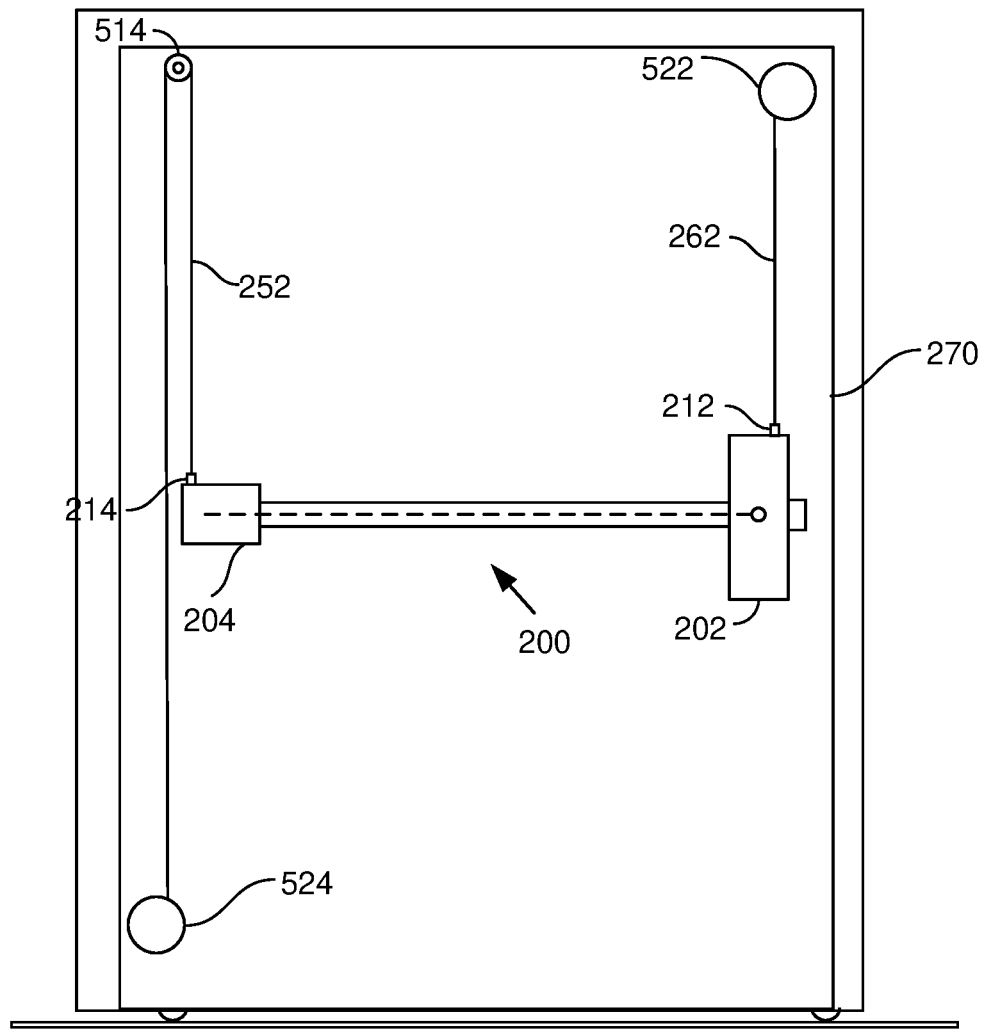
FIGS. 4A-4B illustrate a cross-sectional, side view and a perspective view, respectively of a lift mechanism of the imaging system of FIG. 1, according to an implementation of the disclosure.
Figure 4B:
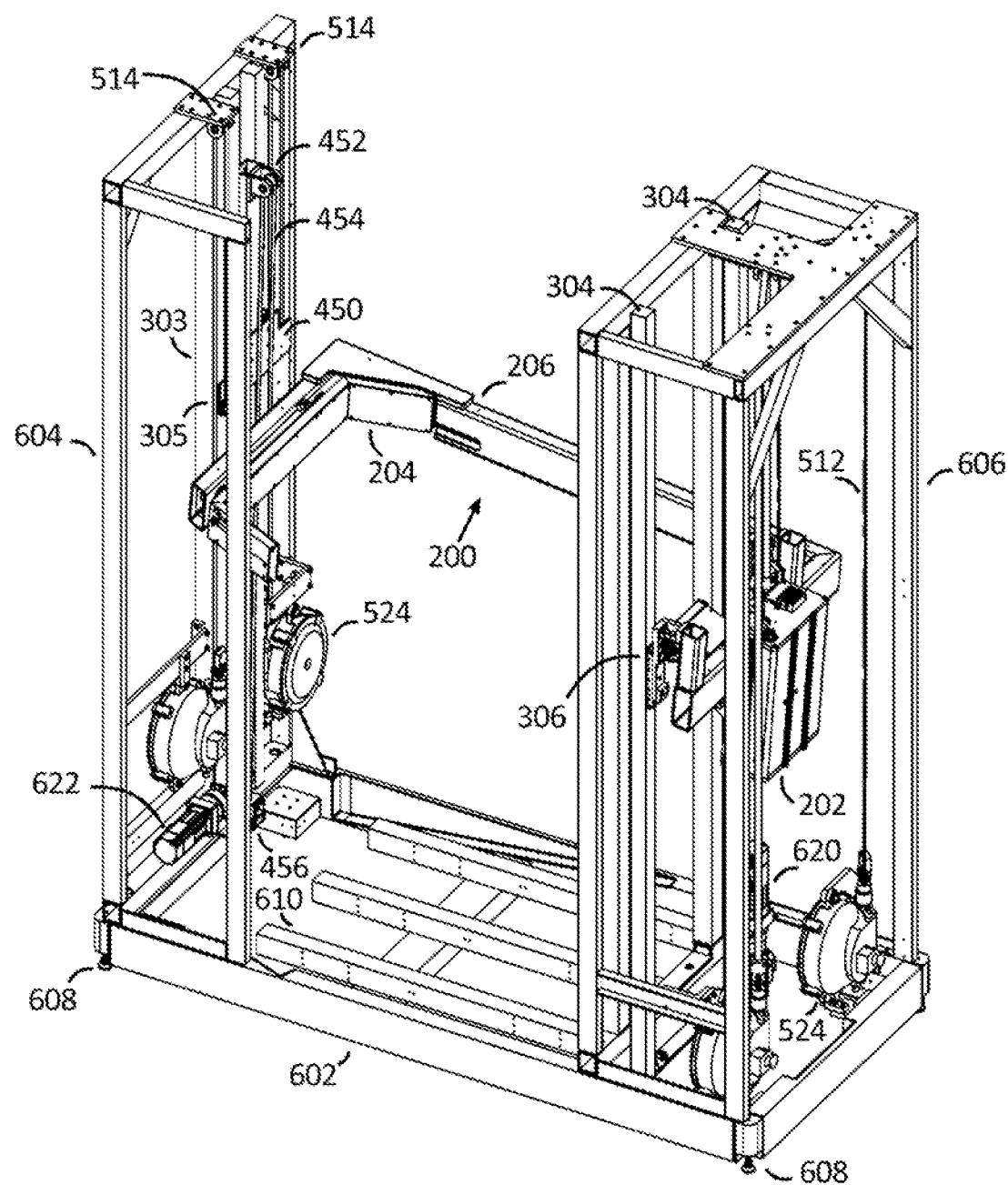

In some embodiments, the one or more counterweight devices may be configured to balance and/or maintain an upward pressure on the X-ray assembly 200 as the X-ray detector 204 and the X-ray source 202 are translated during the imaging process. An example imaging system having a form factor that is smaller than conventional imaging systems in which a lift mechanism comprises one or more balancing devices to facilitate movement of an X-ray assembly may be implemented as illustrated in FIGS. 4A-4B. FIG. 4A provides a cross-sectional, side view of the lift mechanism of the imaging system 100. FIG. 4B provides a perspective view of the lift mechanism of the imaging system 100.

In some embodiments, as illustrated in FIG. 4A, the lift mechanism may comprise one or more cables supporting the X-ray assembly 200 and interconnected with one or more balancing devices. For example, a cable 252, attached to the X-ray detector 204, may be threaded through a pulley 514 and extend downwardly to interconnect with a balancing device 524. Similarly, cable 262, attached to the X-ray source 202, may be interconnect with a counterweight device 522.

The one or more balancing devices may comprise a tension adjustment mechanism configured to control the requisite force to pull the cables connected to the balancing devices. For example, the force required to raise or lower the X-ray source 202 and the X-ray detector 204 may be controlled via the tension adjustment mechanism. In this example, each of the balancing devices 524, 522 may have a tension adjustment mechanism used to control the requisite force to pull the cables 252, 262, respectively. As an alternative embodiment, the tension adjustment mechanism may be configured to just hold the X-ray assembly 200 suspended. In some embodiments, the one or more balancing devices may comprise a manual adjustment mechanism, such as a screw adjustment mechanism, configured to manually adjust the requisite force settings.

In some embodiments, the one or more balancing devices may be mounted at the bottom of the frame of the imaging system 100. As alluded to earlier, one or more cables may support the X-ray source 202 and the X-ray detector 204 by running upwardly over one or more pulleys and extending downwardly to connect with one or more balancing devices. For example, one or more cables may be attached to the X-ray detector 204, run over one or more pulleys and interconnect with two balancing devices mounted on the on the X-ray detector 204 side of the imaging system 100. Similarly, the X-ray source 202 may be supported by one or more cables running over one or more pulleys and interconnecting with two balancing devices on the X-ray source 202 side of the imaging system 100. In this example, the four balancing devices may be configured to support the weight of the X-ray assembly 200 during the translational movement necessitated by the imaging process.

In some embodiments, each of the one or more balancing devices can be constructed or configured similarly to a tool balancer. For example, tool balancers may include devices manufactured by Nasco Industries, such as model TBJ-1522. In some embodiments, these balancing devices may employ rotary springs in conjunction with a tapered cable drum to provide a near constant force on a cable, regardless of the extension.

For example, and as illustrated in FIG. 4B, four balancing devices 524 may be configured to support the weight of the X-ray assembly 200 (illustrated in FIG. 2A) during the translational movement necessitated by the imaging process. As alluded to earlier, the four balancing devices 524 may be mounted at the bottom of the frame of the imaging system 100. For example, the four balancing devices 524 may be mounted near the base frame 602.

As previously noted, the imaging system may comprise the frame surrounded by a housing. In some embodiments, the frame may further comprise a number of individual support frames. For example, the imaging system 100 may comprise a base frame 602, an X-ray detector 204 side upright frame 604, and an X-ray source 202 side upright frame 606. In some embodiments, the base frame 602, the X-ray detector 204 side upright frame 604, and the X-ray source-side upright frame 606 may be formed using a welded aluminum construction.

As previously noted, the one or more cables may support the X-ray source 202 and the X-ray detector 204 by running upwardly over one or more pulleys and extending downwardly to connect with one or more balancing devices. For example, the four balancing devices 524 may be configured to support cables 512 running over four pulleys 514. In some embodiments, cables 512 may be attached to the X-ray detector 204, run over pulleys 514 and interconnect with two balancing devices 254 mounted on the on the X-ray detector 204 side of the imaging system 100. Similarly, the X-ray source 202 may be supported by cables 512 which may attach to the connecting member 206 near the x-ray source 202, thereby supporting some of the weight of X-ray assembly.

In some embodiments, the cables 512 running downward from the pulleys 514, may attach to a vertical member 450. The vertical member 450 may be configured to support a pulley 452. In some embodiments, a cable 454 may extend from a rigid mount 456 near the base frame 602. For example, the cable 454 may run upward over a pulley 452, and then downward attaching to the connecting member 206 near the X-ray detector 204. In some embodiments, the vertical member 450 may be attached to movable slides 305 of two vertically mounted linear actuators 303. In some embodiments, the connecting member 206 may be attached to movable slides 306 of two vertically mounted linear actuators 304.

In some embodiments, the balancing devices 524 may be configured to support the X-ray imaging assembly on the X-ray detector 204 side, by directly supporting the pulley 452 and cable 454. By directly supporting the pulley 452 and the cable 454, the balancing devices 524 in turn support the X-ray assembly. By using four balancing devices 524 to support the weight of the X-ray assembly, the imaging system 100 can use four linear actuators (e.g., 303, 304) to provide vertical movement of the X-ray imaging assembly.

In some embodiments, the imaging system 100 may comprise one or more components to stabilize the imaging system 100 and ensure the imaging system 100 is level with the floor on which it is standing. For example, the imaging system may comprise four leveling feet 608 configured to support the base frame 602. In some embodiments, the leveling feet 608 may be configured to adjust the level of the imaging system 100.

As alluded to earlier, the imaging system 100 may comprise the floor 116 affixed to the interior surface of the base assembly 112, illustrated in FIG. 1. Referring now to FIG. 4B, the imaging system 100 may comprise one or more components configured to support the floor on which the subject stands during the imaging process. For example, one or more support member 610 may be attached to the base frame 602 and provide support for the floor.

Synchronized Movement

In some embodiments, the lift mechanism, as described above, is configured to raise the X-ray assembly 200 in a synchronized fashion. That is, during the imaging process the movement of the X-ray source 204 is synchronized with the movement of and the X-ray detector 204. By synchronizing the movement of the X-ray source 204 and the X-ray detector 204, the fan-beam of X-rays 208 is at the same vertical elevation as the active area 210 of the x-ray detector 204 during the imaging process. As alluded to earlier, the connecting member 206 that connects the X-ray source 204 and the X-ray detector 204 is configured to provide additional stability and ensure alignment between the X-ray source 202 and the X-detector 204 during this synchronized movement.

Independent Movement

In some embodiments, the lift mechanism is configured to raise and lower the X-ray source 202 independently of the X-ray detector 204. For example, the lift mechanism raises and lowers the X-ray detector 204 by energizing the motor 256 which powers the linear actuator that actuates and translates the movement of cable 252 which threads on the pulley 254 for actuating translation of the X-ray detector 204. Similarly, the lift mechanism raises and lowers the X-ray source 202 by energizing the motor 268 which powers the linear actuator that actuates the translates the movement of cable 262 which threads on the pulleys 264, 266 for actuating translation of the X-ray source 202.

Further, as alluded to earlier, by virtue of using a single attachment point and a single linear actuator, conventional imaging systems and thus cannot provide tilting of the individual imaging components (e.g., the X-ray source and the X-ray detector). Because the X-ray source and the X-ray detector must be aligned during the imaging process, the X-ray source must be moved to the uppermost part of the frame. By virtue of having to move the X-ray source to the very top, conventional imaging systems are required to be sized to accommodate the height range traversed by both the X-ray source and the X-ray detector which contributes to the height of the imaging system. Accordingly, the overall height of the conventional imaging system is greater than that of a standard doorway, which prevents this imaging system from being transportable through a standard doorway without extensive disassembly and mechanical lifting equipment. Additionally, using a single linear actuator to raise and lower the X-ray assembly requires a much larger connecting member, as alluded to earlier, which contributes to the form factor of the imaging system.

In contrast, as alluded to above, the X-ray source 202 may move within the vertical path having the first height range, whereas the X-ray detector 204 may move with the X-ray source 202 but within the vertical path having the second height range that exceeds that of the first height range. By virtue of the independent actuation of the X-ray source 202 and the X-ray detector 204, the X-ray source 202 can be angled or tilted towards the X-ray detector 204 during the imaging process. Accordingly, rather than moving the X-ray source 202 to the lowermost or uppermost part of the imaging system 100 illustrated in FIG. 1, the X-ray source can be angled such that the emitted beam of X-ray is directed toward the X-ray detector 204 even if the X-ray source 202 is lower or higher than the X-ray detector 204. This allows the imaging system 100 to maintain its reduced dimensions which contributes to the overall small form factor of the imaging system 100.

Figures 5A, 5B:
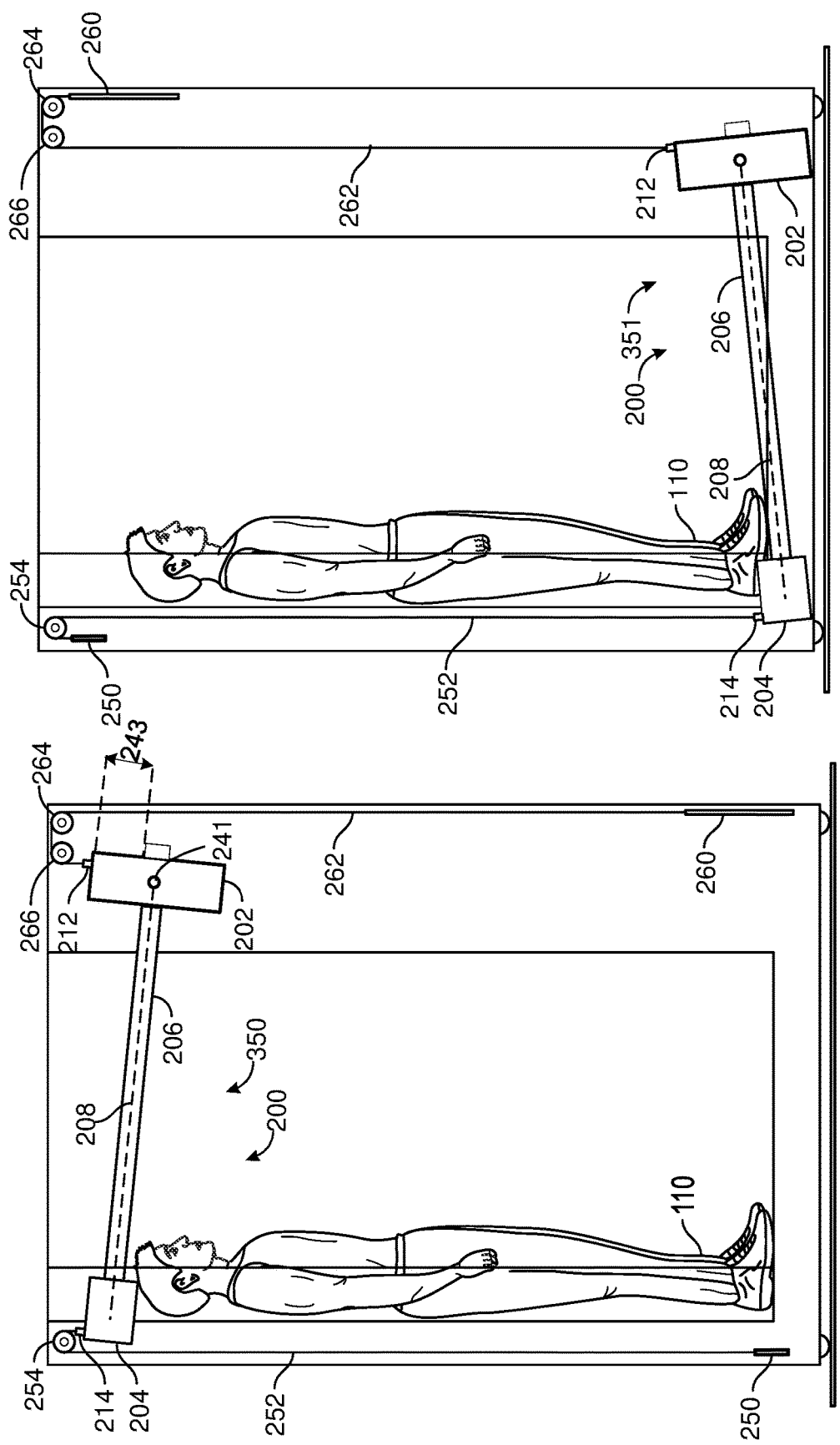
FIGS. 5A-5B illustrate a cross-sectional, side view of an X-ray source and an X-ray detector of the imaging system of FIG. 1 during an imaging process, according to an implementation of the disclosure.

An example imaging system having a form factor that is smaller than conventional imaging systems in which an X-ray source is translated vertically independently of an X-ray detector may be implemented as illustrated in FIGS. 5A-5B. FIG. 5A provides a cross-sectional, side view of the imaging system 100 with an X-ray source and an X-ray detector in a raised position. FIG. 5B provides a cross-sectional, side view of the imaging system 100 with the X-ray source and the X-ray detector in a lowered position.

In some embodiments, by virtue of independent actuation of the X-ray source 202 and the X-ray detector 204, the X-ray source 202 can be angled or tilted towards the X-ray detector 204 during the imaging process. For example, when the X-ray source 202 is in a raised position 350, as illustrated in FIG. 5A, the X-ray source 202 is tilted upward and toward the X-ray detector 204. Similarly, when the X-ray source 202 is in a lowered position 351, as illustrated in FIG. 5B, the X-ray source 202 is tilted downward and toward the X-ray detector 204.

In some embodiments, the X-ray source 202 may comprise a focal spot 241 from which the fan-beam of X-rays 208 is emitted. The focal spot 241 may be substantially equidistant from the edges of the X-ray source 202. For example, the focal spot 241 may be centrally located within the X-ray source 202 and include a distance 243 from either edge of the X-ray source 202.

Angling or tilting the X-ray source 202 upward allows the X-ray source 202 to direct the fan-beam of X-rays 208 at the X-ray detector 204 to scan an uppermost portion of the object without having to raise the X-ray source 202 to the same level as the X-ray detector 204 (i.e., the X-ray source 202 is positioned lower than the X-ray detector 204). As illustrated in FIG. 5A, by virtue of angling or tilting the X-ray source 202 during the imaging process, the beam of X-rays 208, emitted from the focal spot 241, is directed to the X-ray detector 204 without moving the X-ray source 202 to the uppermost portion of the imaging system 100. That is, the distance 243 need not be traveled by the X-ray source 202.

Similarly, angling or tilting the X-ray source 202 downward allows the X-ray source 202 to direct the fan-beam of X-rays 208 at the X-ray detector 204 to scan a lowermost portion of the object without having to lower the X-ray source 202 to the same level as the X-ray detector 204 (i.e., the X-ray source 202 is positioned higher than the X-ray detector 204). As illustrated in FIG. 5B, by virtue of angling or tilting the X-ray source 202 during the imaging process, the beam of X-rays 208, emitted from the focal spot 241, is directed to the X-ray detector 204 without moving the X-ray source 202 to the lowermost portion of the imaging system 100. That is, the distance 243 need not be traveled when the X-ray source 202.

In some embodiments, the degree of tilt of the X-ray source 202 (e.g., approximately 5 to 20 degrees) may only increase a path of the beam of X-rays through the subject's body by a few percent. Because the degree of tilt only slightly increases the X-ray path length, the resulting increase in radiation from the increased path length of X-rays is negligible. In contrast, in some conventional systems, the X-rays enter the subject's body at a 45-degree angle which results in exposing the subject to higher radiation levels.

Referring back to FIG. 2A to illustrate how tilting the X-ray source 202 either upward or downward, allows the imaging system 100 to maintain the form factor smaller than conventional imaging systems. For example, the height 216 of the X-ray detector 204 is approximately 10 cm, while the height 248 of the X-ray source 202 is approximately 40 cm. As alluded to earlier, by virtue of angling or tilting the X-ray source 202 during the imaging process either upward or downward, the height 132 of the imaging system 100 illustrated in FIG. 1 is only affected by the height 216 of the X-ray detector 204. Accordingly, the imaging system 100 is able to maintain a lower height 132 of which results in the imaging system 100 to be transported through a standard doorway.

Referring back to FIGS. 5A-5B, in some embodiments, the motors 256, 266 used for raising and lowering of the X-ray assembly 200 during the imaging process from the lowermost position 351 to the uppermost position 350 may be configured to operate at different rates.

In some embodiments, the imaging system 100 may comprise a motion control unit (not shown) configured to adjust individual rates at which the motors 256, 266 operate. For example, the individual rates at which the motors 256, 266 operate may be adjusted by one or more microprocess controllers. By controlling the rates at which the motors 256 266 operate, the imaging system 100 may raise and lower the X-ray assembly 200 with no rotation, with an accompanying rotation in one direction, with an accompanying rotation in an another (e.g., opposite) direction, or with any combination accompanying rotation.

In some embodiments, the motor 254 powering the movement of the X-ray detector 204 may operate at a rate of approximately twelve to fifteen percent higher than the motor 266 powering the movement of the X-ray source 202. During the imaging process, and as illustrated in FIGS. 5A-5B, the difference in rates at which the motors 254, 266 operate results in the X-ray detector 204 traversing a distance that is approximately twelve to fifteen percent greater than the distance of the X-ray source 202 in the same amount of time. That is because, the distance that X-ray detector must traverse during the imaging process is approximately 15 percent greater than the distance the X-ray source 202 must traverse.

Extension Mechanism

As alluded to earlier, maintaining the small form factor can be a factor for the transportability of the imaging system. Of particular importance is ability to fit the imaging system through standard-sized doorways without extensive disassembly. However, as alluded to earlier, some doorways (e.g., prison doorways) may have one or more dimensions that are smaller than that of a standard-size doorway (e.g. less than the 200 cm). Another factor is the ability to image a person that may be taller than the standard-sized doorway. That is, the imaging system, in accordance with one embodiment, has one height during transportation and another height when imaging a person whose height is less than the doorway through which the imaging system is being transported. One way to accommodate both is by using a lift mechanism that can effectuate a range of movement that exceeds the height of the imaging system to temporarily raise the X-ray source and the X-ray detector. For example, the lift mechanism can be configured to raise the X-ray source and the X-ray detector during the imaging process to image a person whose height exceeds that of the imaging system by utilizing one or more mechanisms (e.g., telescoping, scissor, etc.).

FIGS. 6A-6B illustrate an example imaging system 600 (which may be an embodiment of imaging system 100) having a form factor that is smaller than conventional imaging systems in which an X-ray source and an X-ray detector joined by a connecting component are translated vertically within the frame of the imaging system 600 via individual vertical paths of varying height range may be implemented as illustrated in FIGS. 6A-6B. FIG. 6A provides a cross-sectional, side view of the imaging system 600 with an X-ray source and an X-ray detector in a lowered position. FIG. 6B provides a cross-sectional, side view of the imaging system 100 with the X-ray source and the X-ray detector in a raised position.

In some embodiments, the lift mechanism, as described above, is configured to raise the X-ray source 202 within a vertical path having a first height range and raise the X-ray detector 204 within a vertical path having a second height range which exceeds the first height range. In some embodiments, the vertical path within which the X-ray detector 204 is raised may exceed the height of the imaging system 100. By virtue of the vertical path of the X-ray detector 204 exceeding the height of the imaging system 600, allows the imaging system 600 to perform the imaging of a subject that may otherwise be impossible due to height constrains of the imaging system 600 (e.g., the height of the person 101 exceeding the height 132 of the imaging system 100 illustrated in FIG. 1).

For example, at the beginning of the imaging process, the X-ray assembly 200 (e.g., the X-ray source 202 and the X-ray detector 204), illustrated in FIG. 2A, is in a lowermost position 352, as illustrated in FIG. 6A. Similarly, at the end of the imaging process, the X-ray assembly 200 is in an uppermost position 350, as illustrated in FIG. 6B. Accordingly, the imaging system 600 may be configured to perform imaging of a person 110 whose height exceeds the height 492 of the imaging system 100.

In some embodiments, the lift mechanism may be configured to raise the X-ray detector 204 beyond the height of a frame of the imaging system 600 (e.g., to the uppermost position 350) only during the imaging process. That is, once the imaging process is completed, the X-ray detector 204 is lowered and returned to the lowermost position 352. By virtue of raising the X-ray detector 204 above the height of the imaging system 600 only during the imaging process, allows to transport the imaging system 600 through standard-sized doorways, as the height 492 of the imaging system 600 is not affected by this extension.

In some embodiments, the lift mechanism may comprise one or more movable slides, one or more motors, one or more linear actuator devices, one or more pulleys, one or more cables, one or more counterweight devices, a rigid mount, and/or other components configured to lower and raise the X-ray assembly 200 within the frame of the imaging system 600.

In some embodiments, the X-ray source 202 may be coupled to a movable slide 306. For example, the lift mechanism raises and lowers the X-ray source 202 by energizing a motor which powers a linear actuator device 304 which actuates the movable slide 306 coupled to the linear actuator device 304. That is, the lift mechanism raises the X-ray source 202 from a first position 368 (illustrated in FIG. 6A) at the beginning of the imaging process to a second position 366 (illustrated in FIG. 6B) at the end of the imaging process by energizing a motor which powers a linear actuator device 304 which actuates and translates the movement of a movable slide 306 coupled to the linear actuator device 304.

In some embodiments, the X-ray detector 204 may be coupled to a cable 454. For example, cable 454 may comprise a first terminus at an attachment point mounted on the X-ray detector 204. In some embodiments, the cable 454 may be threaded through a pulley 452 and extend downwardly to interconnect with a rigid mount 456.

In some embodiments, the rigid mount 456 may be mounted within a linear actuator device 303 comprising a non-moving frame. In yet other embodiments, the rigid mount 456 may be mounted within any stationary location within the frame of the imaging system 600.

In some embodiments, the pulley 452 may be mounted to a vertical member 450 positioned within the frame of the imaging system 100. For example, the pulley 452 may be mounted to an upper end of a vertical member 450, while the lower end of vertical member 450 may be rigidly attached to a movable slide 305 of the linear actuator 303. In some embodiments, the vertical member 450 may be approximately 38 cm long.

In some embodiments, the lift mechanism raises the X-ray detector 204 from a first position 480 (illustrated in FIG. 6A) at the beginning of the imaging process to a second position 482 (illustrated in FIG. 6B) by energizing a motor which powers the linear actuator 303 which actuates and translates the movement of the movable slide 305 coupled to the linear actuator device 303.

In some embodiments, at the beginning of the imaging process, the movable slide 305 is positioned at a first position 470, the pulley 452 is positioned a first position 471, and the X-ray detector 204 is positioned at a first position 480. As alluded to above, during the imaging process the lift mechanism raises the X-ray detector 204 by translating the movable slide 305 from the first position 470 to a second position 472. As the movable slide 305 is translated, the pulley 452 (mounted to a vertical member 450 which is rigidly attached to the movable slide 305, as explained above) moves from the first position 471 to a second position 473.

By virtue of powering the linear actuator 303, which vertically translates the movable slide 305 from the first position 470 to the second position 472, the pulley 452 is forced to move from the first position 471 to the second position 473. The translational movement of the movable slide 305 in turn lifts the X-ray detector 204 from the first position 480 to the second position 482. By virtue of the lift mechanism, the distance which the movable slide 305 traverses is approximately 107 cm while the distance that the X-ray detector 204 traverses is approximately 214 cm. Accordingly, the distance traversed by the X-ray detector 204 is approximately double that of the movable slide 305.

Automated Alignment

In some embodiments, prior to initiating the imaging process, the imaging system 100 of FIG. 1 may be configured to align the X-ray detector 204 with the X-ray source 202. For example, the X-ray detector 204 may be positioned in a lowermost position 351, as illustrated in FIG. 4B. The lift mechanism, as described above, actuates the X-ray detector 204 independently of the X-ray source 202 until the beam of X-rays emitted by the X-ray source 202 is intercepted and absorbed by the one or more photodiode arrays of the X-ray detector. For example, the lift mechanism may comprise one or more linear actuators mounted at each end of the X-ray detector 204 configured to move the X-ray detector 204 with respect to the connecting member 206. The translational movement of the X-ray detector 204 may be slight and may include moving at least one end of the X-ray detector 204. In some embodiments, the lift mechanism is configured to rotate the X-ray detector 204 relative to a horizontal axis.

In some embodiments, the imaging system 100 is configured to detect a signal comprising a signal strength corresponding to one or more photodiodes within the one or more photodiode arrays of the X-ray detector 204 absorbing a particular amount of radiant energy emitted by the X-ray source 202. That is, the stronger the signal the greater the amount of radiant energy is absorbed. A stronger signal is indicative that the alignment between the X-ray detector 204 and the X-ray source 202 is likely achieved. The X-ray detector 204 may be translated (e.g., raised or lowered) until the signal strength of a threshold level is detected. In some embodiments, this process may be repeated iteratively until the X-ray detector 204 and the X-ray source 202 are aligned.

In some embodiments, once the desired signal strength is reached, the imaging system 100 is configured to note the alignment between the X-ray detector 204 and the X-ray source 202 that resulted in the desired signal strength. That is, the imaging system 100 is configured to utilize the resulting alignment between the X-ray detector 204 and the X-ray source 202 during the imaging process.

Identity Verification

As alluded to earlier, imaging system 100 may be used to detect concealed security threats on persons entering high security areas (e.g., airports, prisons, etc.). As described above, the imaging system 100 may generate images that reveal concealed threats in or on a person's body. Because these images may later be introduced as physical evidence in various government actions instituted against the subject, management of acquired information (e.g., image data), including access and chain-of-custody issues must be considered. Of particular concern, is ability to confirm and/or verify subject's identity using image data alone. For example, the subject may subsequently dispute that the image showing a concealed threat is indeed him or her.

In some embodiments, the imaging system 100 of FIG. 1 may include one or more features configured to assist in personal identity verification, alluded to above. For example, the imaging system 100 may be configured to capture information related to the subject. The information may include visual information (e.g., image, video, audio), biometric information (e.g., fingerprint, facial recognition, retina scan, etc.), and/or other similar information.

In some embodiments, one or more input devices configured to capture subject-related information may be coupled to the imaging system 100. For example, the one or more input devices may include a biometric input device and a visual input device. In some embodiments, the biometric input device may comprise a digital device, such as a fingerprint scanner or retinal scanner configured to obtain a scanned image of a subject's retina. The visual input device may comprise a device such as an image camera, and/or other device configured to capture information, including but not limited to visual information, video information, and audio information.

In some embodiments, the one or more input devices may be coupled to or integrated with the control panel 124 and/or other interface within the imaging system 100. For example, prior to entering the interior space 119 of the imaging system 100, a person 110 may be positioned in front of the control panel 124 coupled to an image camera such that an image associated the person 110 may be captured. In some embodiments, the one or more input devices may be integrated into the one or more components of the housing of the imaging system 100 (e.g., the X-ray source compartment 120). For example, a visual input device may capture a video of a subject contemporaneously with the image data acquisition during the imaging process.

In some embodiments, information generated by the imaging system 100, including image data and information captured by the one or more input devices may be marked, timestamped, annotated, and/or otherwise processed such that all information generated by the imaging system 100 can be synchronized, aligned, annotated, and/or otherwise associated therewith. For example, video information captured by an image sensor of the input device may be synchronized with image data generated by the X-ray detector. Subject-related information generated by the one or more input devices (and/or information based thereon) may be stored and/or transferred in electronic files. Capturing subject-related information and associating it with the image data, as alluded to above, may allow to verify subject's identity. For example, while the image data alone may not be enough to conclusively establish identity of the subject, using a subject's image in conjunction with the image data may provide the necessary confirmation.

Figure 7:
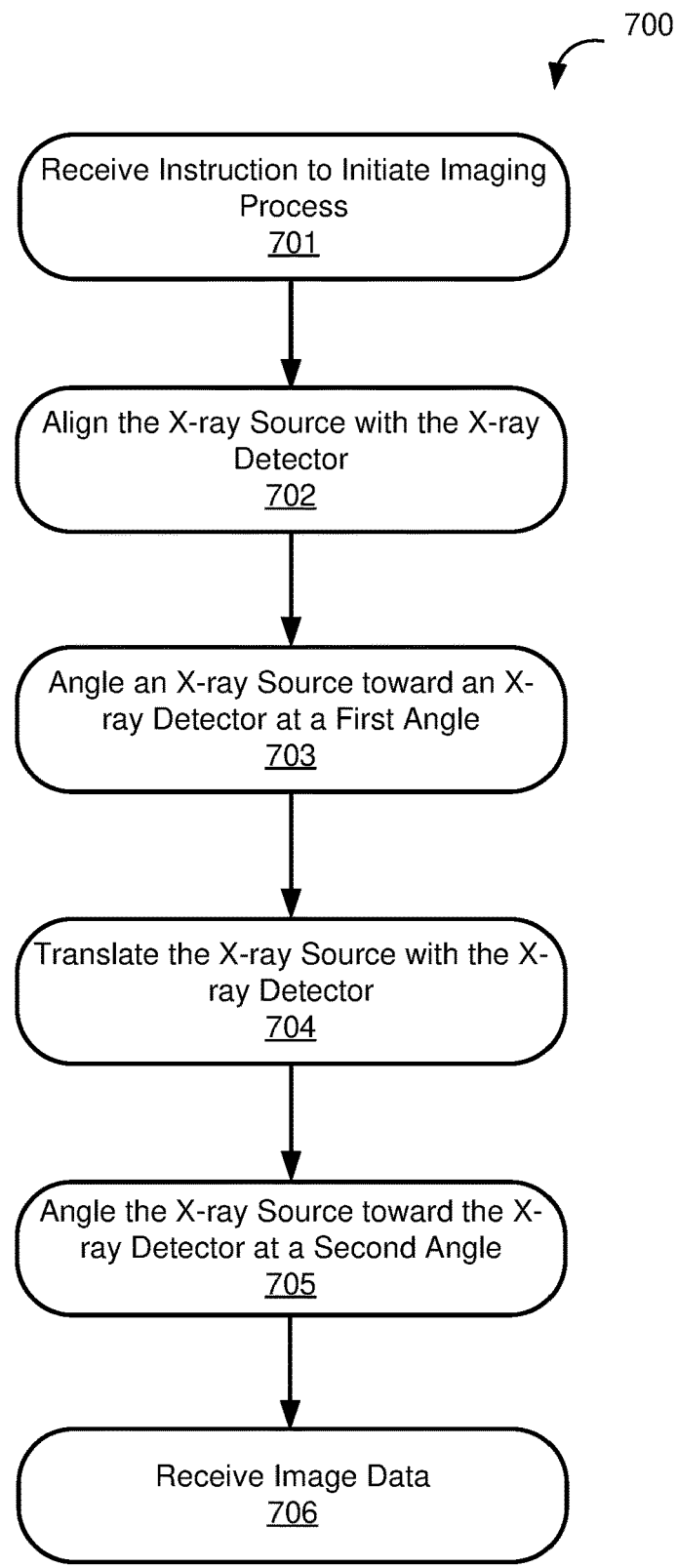
FIG. 7 illustrates a process of performing an imaging scan, according to an implementation of the disclosure.

FIG. 7 is a flow chart illustrating example operations that can be performed to actuate of a lifting mechanism to effectuate an imaging process. In some implementations, the operations may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operation in response to instructions stored electronically on one or more electronic storage mediums. The one or more processing devices may include one or more devices configured through hardware, firmware, and/or software to be specifically designed for execution of one or more of the operations.

In an operation 701, a control signal or instruction to initiate the imaging process is received. For example, as described above, an imaging process can be initiated by a user-initiated command entered through a control panel 124 or other interface. The user command made via the control panel 124 is translated to imaging process initiation within the imaging system 100.

In an operation 702, a step to ensure an X-ray source is in geometric alignment with an X-ray detector is performed. For example, as described above, the X-ray detector 204 is independently actuated to be vertically translated in either direction to intercept a fan-beam of X-rays 208 emitted by the X-ray source 202. As the X-ray detector 204 intercepts the fan-beam of X-rays, the X-ray detector 204 may detect a signal of a particular signal strength. The X-ray detector 204 may be translated iteratively until a signal of a threshold signal strength is detected, which suggests that the X-ray source 202 and the X-ray detector 204 are in optical alignment.

In an operation 703, the X-ray source and the X-ray detector are independently actuated to move to a position ready to with each other to obtain signals associated with imaging a lowermost portion of a subject. For example, as described above, to obtain signals associated with imaging the lowermost portion of the subject, the X-ray detector 204 is positioned at a first level while the X-ray source 202 is positioned at a second level, the second level being higher than the first level. While at the second level, the X-ray source 202 is angled downwardly so as to emit the beam of X-rays toward the X-ray detector 204 ready to obtain the signals associated with imaging the lowermost portion of the subject.

In an operation 704, the X-ray source and the X-ray detector are moved in conjunction with each other such that the X-ray source is translated vertically at a first rate and the X-ray detector is translated vertically at a second rate relative to each other to obtain signals associated with imaging a subject, with the exception of the lowermost and uppermost portions of the subject. For example, as described above, the X-ray detector 204 is raised by energizing a motor 256 which powers a linear actuator that actuates and translates the movement of a cable 252 attached to the X-ray detector 204 which threads on a pulley 254 for actuating translation of the X-ray detector 204. Similarly, the X-ray source 202 is raised by energizing a motor 268 which powers a linear actuator that actuates and translates the movement of cable 262 which threads on pulleys 264, 266 for actuating translation of the X-ray source 202.

In an operation 705, the X-ray source and the X-ray detector are independently actuated to end the translation 704 at position suitable to obtain signals associated with imaging an uppermost portion of a subject. For example, as described above, to obtain signals associated with imaging the lowermost portion of the subject, the X-ray detector 204 is raised to a third level while the X-ray source 202 is raised to a fourth level, the fourth level being lower than the third level. While at the fourth level, the X-ray source 202 is angled upwardly so as to emit the beam of X-rays toward the X-ray detector 204 to obtain the optical signals associated with imaging.

In an operation 706, image data corresponding to an image of the subject scanned during the imaging process is received. For example, as described above, during the imaging process optical signals generated by the photodiode array within the X-ray detector 204 are converted into electrical signals. The electrical signals result in image data transmitted via analog and/or digital electronic circuits.

Figure 8:
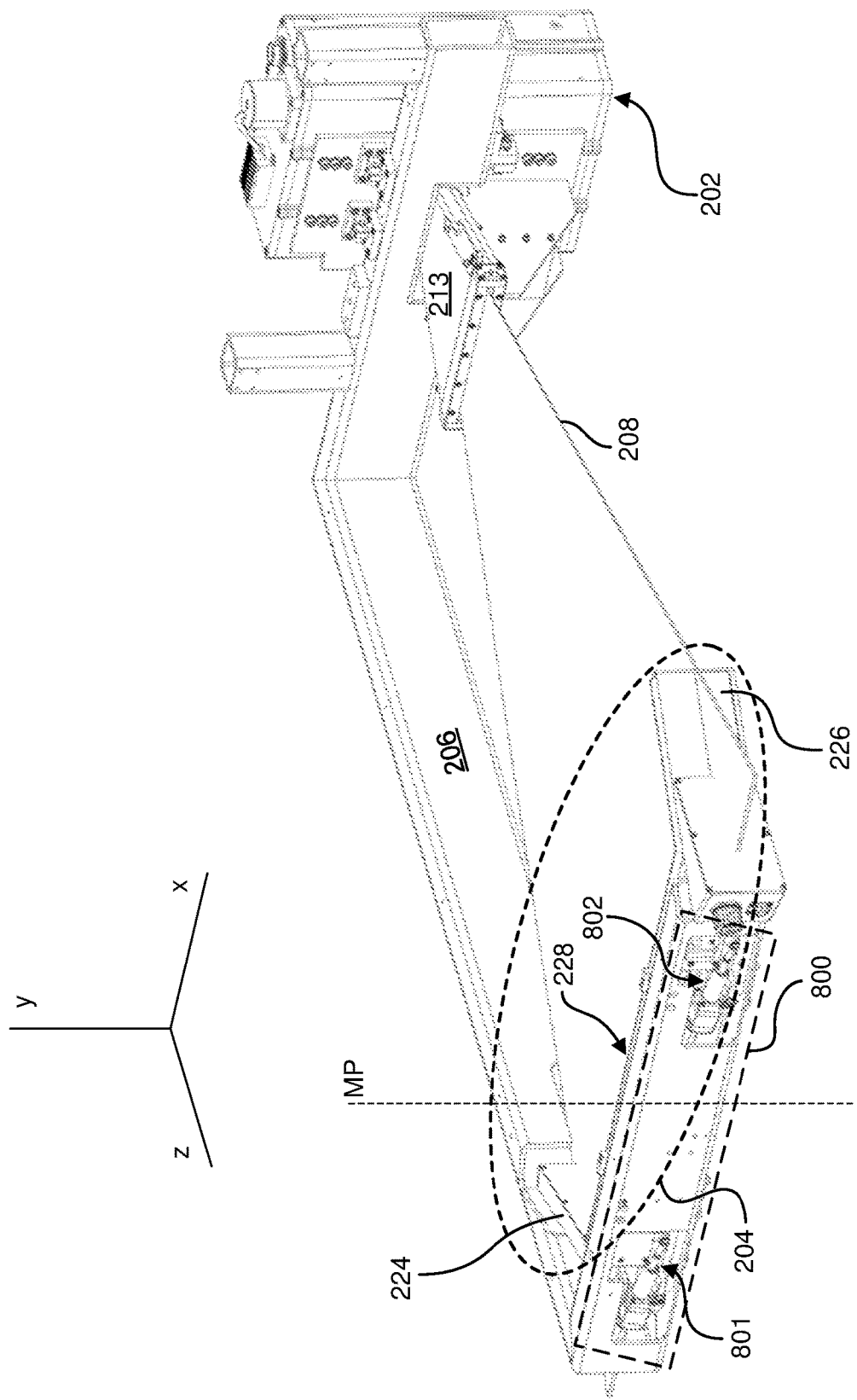
FIG. 8 illustrates an aligned state of the output of the collimator and the active region of the X-ray detector array, wherein the fan-beam of X-rays is properly aligned with the X-ray detector in accordance with embodiments of the technology disclosed herein.

As discussed above with respect to FIG. 2A, the at least one collimator 213 is configured to collimate the beams of X-rays from the X-ray source 202 into a fan-beam of X-rays 208 corresponding to the dimensions of the X-ray detector 204. Collimating the beams X-rays in this way enables a decreased size of the X-ray detector 204 by confining the X-rays to a narrow active area. Accordingly, the alignment between the fan-beam of X-rays 208 and the narrow active area (i.e., the photodiode array 210) is important to ensure accurate imaging. FIG. 8 illustrates an aligned state of the output of the collimator 213 and the active region of the X-ray detector array 200, wherein the fan-beam of X-rays 208 is properly aligned with the X-ray detector 204. In various embodiments, the active area may extend along the X-ray detector 204 and onto each of the first member 224 and the second member 226. When aligned, the fan-beam of X-rays 208 is also detected by the portions of the photodiode array (not shown in FIG. 8) extending onto the first member and the second member.

If the fan-out beam of X-rays 208 is not properly aligned with the active area of the X-ray detector 204, inaccurate or partial images may be obtained, limiting the effectiveness of the imaging system. In various embodiments, the misalignment occur in one or more directions. As a non-limiting example, the fan-out beam of X-rays 208 may be rotated about the x-axis such that the fan-out beam 208 intersects with the X-ray detector assembly 204 at a point above or below the active area of the X-ray detector 204, and/or the fan-out beam of X-rays 208 may be rotated about the z-axis such that the fan-out beam 208 intersects with the X-ray detector assembly 204 above the active area 210 on a first side of the X-ray detector assembly 204 and below the X-ray detector assembly 204 below the active area 210 on a second side of the X-ray detector assembly 204. In various embodiments, the first side of the X-ray detector assembly 204 can extend from the midplane MP of the back member 228 to a distal end of the first member 224 and the second side of the X-ray detector assembly 204 can extend from the midplane MP of the back member 228 to a distal end of the second member 226.

To account for this type of potential misalignment, a calibration system 800 can be disposed within the connecting member 206 and configured to move the X-ray detector assembly 204 with respect to the connecting member 206. In the illustrated embodiment, the calibration system 800 comprises a first calibration assembly 801 and a second calibration assembly 802. Each of the calibration assemblies 801, 802 are configured to move the X-ray detector assembly 204 in order to position the active area of the X-ray detector assembly 204 to align with the fan-out beam of X-rays 208 across the entire length of the active area. Although the illustrated embodiment of FIG. 8 shows two calibration assemblies 801, 802 within the calibration system 800, in other embodiments a plurality of calibration actuators can be included depending on the resolution of adjustment required for a particular implementation.

Figure 9A:
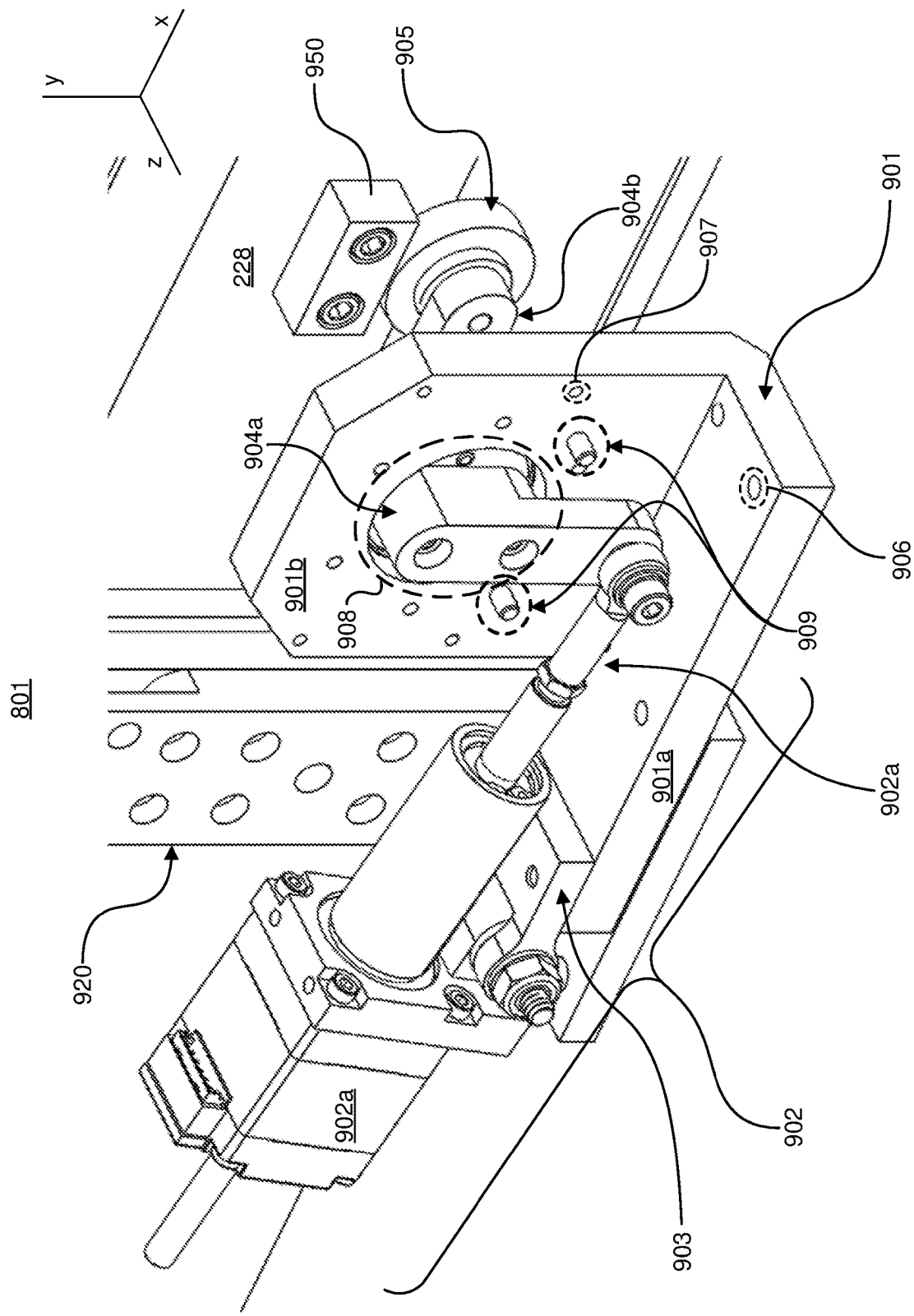
FIG. 9A illustrates an example first calibration assembly in accordance with embodiments of the technology disclosed herein.

FIG. 9A is a closer view of an example first calibration assembly 801 depicted in FIG. 8. Although discussed with respect to the first calibration assembly 801, the discussion is applicable to the second calibration assembly 802 or other calibration actuators included within the calibration system. For ease of illustration, the connecting member 206 of FIG. 8 is omitted to make it easier to see the different components of the first calibration assembly 801. Although omitted, the first calibration assembly 801 is disposed within the interior void of the connecting member 206. In various embodiments, the first calibration assembly 801 can comprise a base plate 901, a calibration actuator 902, a lever arm 904, and a detector mover 905. The base plate 901 can be used to secure the first calibration assembly 801 to an interior surface of the bottom plate of the connecting member 206 (not shown in FIG. 9A). In various embodiments, the base plate 901 can comprise a bottom portion 901a and a vertical portion 901b. The bottom portion 901a can include a plurality of connector openings 906 configured to enable a plurality of fasteners to secure the bottom portion 901a of the base plate 901 to the interior surface of the bottom side of the connecting member 206. The vertical portion 901b can include a plurality of connector openings 907 configured to enable a plurality of fasteners to secure the vertical portion 901b to a detector side of the connecting member 206, the detector side being the side of the connecting member 206 facing the X-ray detector assembly 204. In various embodiments, the bottom portion 901a and the vertical portion 901b can be integrated into a single base plate 901, while in other embodiments the bottom portion 901 and the vertical portion 901b can comprise separate components that together represent the base plate 901.

In various embodiments, the vertical portion 901b can include an opening 908 enabling a first portion 409a of the lever arm 904 to operatively connect to a second portion

409b of the lever arm 904. In various embodiments, the opening 908 can be dimensioned based on the size and design of the lever arm 904 to facilitate a rotational radius of the lever arm 904 when pushed or pulled by the calibration actuator 902. One or more lever arm stops 909 can extend from a surface of the vertical portion 901b into the interior of the connecting member 206, configured to stop the motion of the lever arm 904. In the illustrated embodiment, the opening 908 is depicted as a circular opening, in other embodiments the opening 908 can have lever arm stops integrated therein. As a non-limiting example, the opening 908 can be configured such that the first portion 904a of the lever arm 904 is capable of only rotating along an arc of the opening 908.

A calibration actuator 902 can be configured to move the first portion 904a of the lever arm 904 along a range of distances from a first position to a second position. In various embodiments, the first position can be defined by the a first lever arm stop and the second position can be defined by a second lever arm stop, with the first portion 409a capable of moving between the first position and the second position. In various embodiments, the calibration actuator 902 can comprise a servo motor or other linear actuator, similar to the actuators discussed above with respect to the translational mechanism. A distal end of the push rod 902a of the calibration actuator 902 can be secured to the first portion 904a of the lever arm 904 to transfer the linear motion of the push rod 902a to a rotational motion of the lever arm 904. In some embodiments, the push rod 902a of the calibration actuator 902 can include one or more protrusions (not shown in FIG. 9A) configured to stop the push rod 902a from extending further than necessary to push the first portion 904a of the lever arm 904 to the second position or retract further than necessary to pull the first portion 904a of the lever arm 904 to the first position.

In various embodiments, the calibration actuator 902 can include a motion generator 902b configured to extend or retract the push rod 902a. In various embodiments, the motion generator 902b can be electrical, pneumatic, or hydraulic. A controller (not shown in FIG. 9A) is communicatively coupled to the motion generator 902b and configured to control operation of the motion generator 902b. As a non-limiting example, the controller can be configured to apply one or more control signals to the motion generator 902b to activate either the electrical, hydraulic, or pneumatic actuation components of the motion generator 902b to change the position of the push rod 902a. In various embodiments, the controller can be configured to receive data from one or more sensors (not shown in FIG. 9A) indicative of an orientation of the fan-out beam of X-rays 208. Based on this information, the controller can generate the one or more control signals to move the push rod 902a in order to position the X-ray detector assembly 204. The calibration actuator 902 can be secured to the bottom portion 901a of the base plate 901 by an anchor plate 903. In various embodiments, the calibration actuator 902 may be fixed in position relative to the anchor plate 903, while in other embodiments the calibration actuator 902 may be pivotable around a fastener relative to the anchor plate 903.

When the calibration actuator 902 moves the push rod 902a from the first position to the second position, the lever arm 904 rotates such that the second portion 904b of the lever arm 904 rotates in an upward direction (from a point on the x-axis to a point on the y-axis). The detector mover 905 is configured to contact a detector support 950 disposed on a back side of the back member 228 of the X-ray detector assembly 204. In various embodiments, the detector mover 905 can be configured to maintain contact with the detector support 950 throughout the rotation of the second portion 904b of the lever arm 904. As a non-limiting example, the detector mover 905 can comprise a bearing-based component configured such that the detector mover 905 can rotate around the point of connection with the second portion 904b of the lever arm 904 without changing its operative connectivity to the detector support 950. The motion of the X-ray detector assembly 204 caused by movement of the second portion 904b of the lever arm 904 shall be further discussed with respect to FIGS. 9D-9G.

Figure 9B:
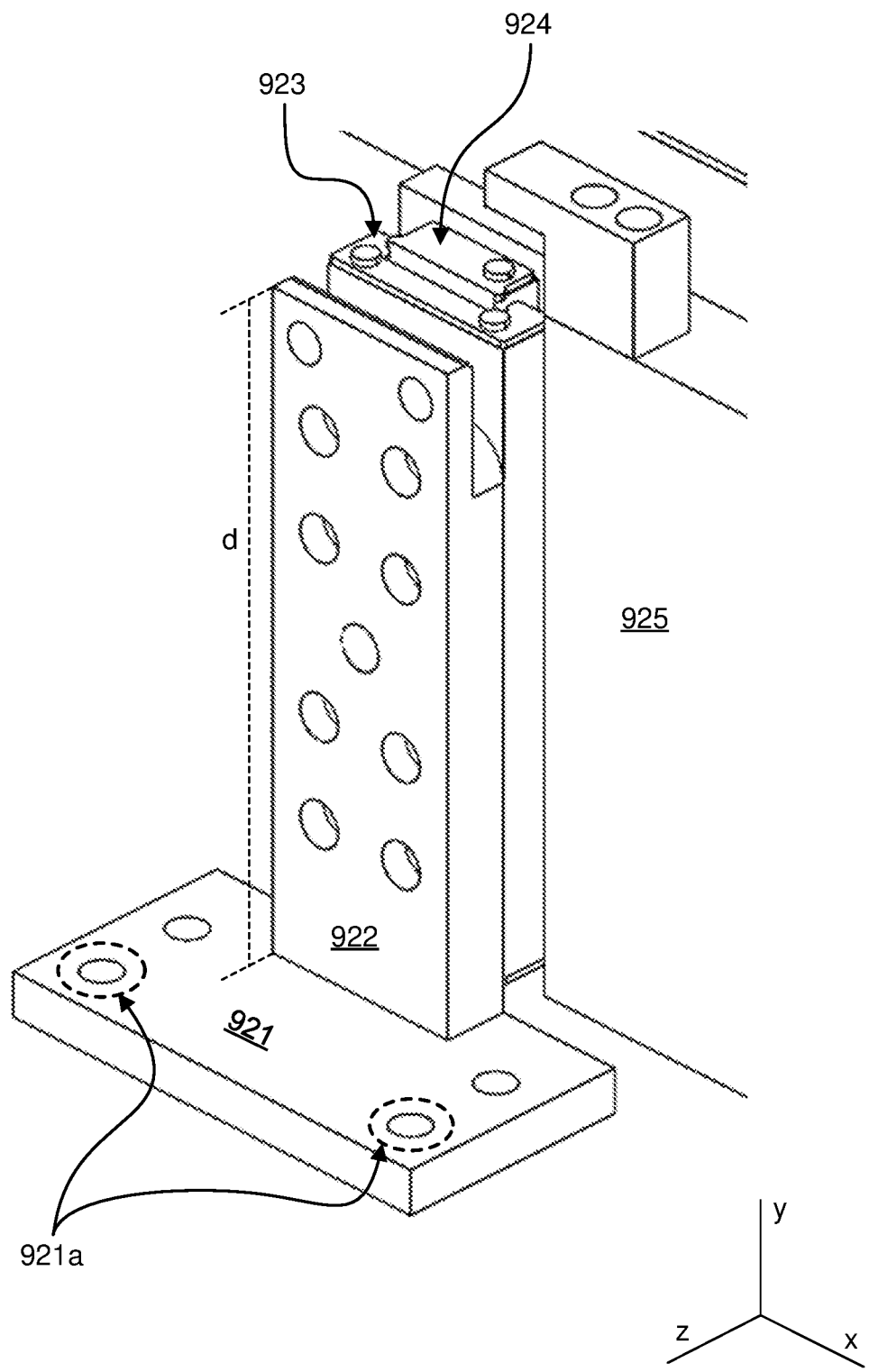
FIG. 9B illustrates an example vertical slider assembly in accordance with embodiments of the technology disclosed herein.

To facilitate the motion of the X-ray detector assembly 204, a vertical slide assembly 920 can be included within the calibration system 800. FIG. 9B illustrates an example vertical slide assembly 920 in accordance with embodiments of the technology disclosed herein. The example vertical slide assembly 920 is provided for illustrative purposes only and should not be interpreted as limiting the scope of the technology to only the depicted embodiment. For ease of discussion, the calibration assembly 801, 802 is omitted from FIG. 9B to enable an easier view of the example vertical slide assembly 920. As shown in FIG. 9B, the vertical slide assembly 920 can comprise a base plate 921, a slide mount 922, a slide track 923, a slider 924, and a detector plate 925. Although discussed with respect to the example vertical slide assembly 920, in various other embodiments one or more additional components van be included which are not explicitly shown in FIG. 9B.

The base plate 921 can include a plurality of connection openings 921a. In various embodiments, the amount of connection openings 912a can be determined based on the size of the base plate 921. The plurality of connection openings 921a are configured to accept one or more fasteners, including but not limited to nuts, bolts, screws, or other types of fasteners. In various embodiments, the base plate 921 can be connected to an exterior surface of the bottom side of the connecting member 206 (not shown in FIG. 9B). A slide mount 922 can be connected to the base plate 921 and configured to extend in the vertical direction (i.e., along the y-axis) a distance d from the base plate 921. In various embodiments, the distance d can be equivalent to a height of a detector-facing side of the connecting member 206, while in other embodiments the distance d can be smaller than the height of the detector-facing side of the connecting member 206. The slide mount 922 can comprise metal, metal alloy, plastic, or other material, of a combination thereof. In various embodiments, the slide mount 922 can be made of a stiff material.

In various embodiments, the slide track 923 can be operatively connected to the slide mount 922. The slide track 923 provides a structure that can be operatively connected to a movable slider (e.g., the slider 924) to facilitate a controlled movement of the slider 924. In various embodiments, the slide track 923 can be secured to the slide mount 922 by one or more methods, including but not limited to fasteners, epoxy, glue, weld, or other securing means. In various embodiments, the slide track 923 can comprise a single integrated component, while in other components the slide track 923 can comprise one or more components that operatively comprise the slide track 923. As a non-limiting example, the slide track 923 can comprise a first rail and a second rail, each separate from each other. The first rail and the second rail can be independently to the slide mount 922. In some embodiments, the slide track 923 can be integrated into the slide mount 922 to comprise a monolithic component. Within the slide track 923, a slider 924 can be inserted such that a portion of the slide track 923 is configured to operatively connect to a portion of the slider 924 such that the slider 924 is secured to the slide track 923. In various embodiments, the slider 924 can comprise one or more channels or grooves disposed on an edge of each side of the slider 924 that are configured to couple to one or more corresponding grooves of the slide track 923.

The slider 924 can be operatively connected to a detector plate 925. The detector plate 925 is configured to operatively connect the calibration system 800 to the back member 228 of the X-ray detector assembly 204. In various embodiments, each vertical slider assembly 920 can have an associated detector plate 925, while in other embodiments the slider 924 of each vertical slider assembly 920 can be connected to the same detector plate 925. In this manner, the movement of the X-ray detector assembly 204 can be constrained to move in the vertical direction (along the y-axis) and not in the horizontal direction (along the x-axis).

Figure 9C:
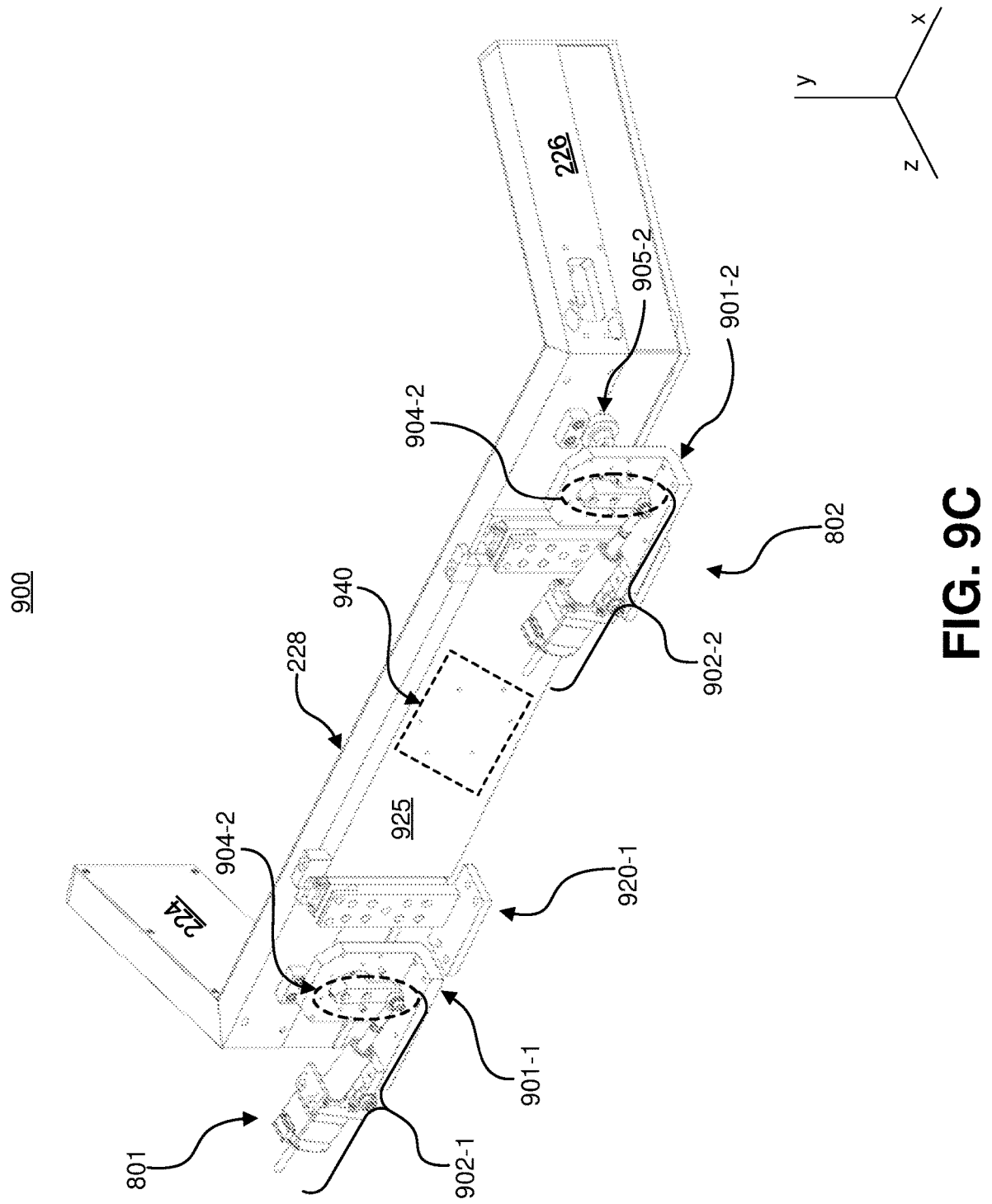
FIG. 9C illustrates an example calibration system assembly in accordance with embodiments of the technology disclosed herein.

FIG. 9C illustrates an example calibration system assembly 900 in accordance with embodiments of the technology disclosed herein. The example calibration system assembly 900 is provided for illustrative purposes only and should not be interpreted as limiting the scope of the technology to the depicted embodiment. The calibration system assembly 900 illustrates the calibration system 800 discussed with respect to FIGS. 8, 9A, and 9B operatively connected to the X-ray detector assembly 204 (comprising the back member 228, first member 224, and the second member 226). As shown in FIG. 9C, each vertical slider assembly 920-1, 920-2 can be operatively connected to a common detector plate 925. In various embodiments, the detector plate 925 can include one or more connection regions 940 configured to provide one or more connector features to secure the back member 228 of the X-ray detector assembly 204 to the detector plate 925.

In various embodiments, the calibration assemblies 801, 802 can be configured in the same orientation. As depicted in FIG. 9C, the first calibration assembly 801 and the second calibration actuator 802 are positioned such that the push rod 902a of the calibration actuator 902 is configured to extend to the right along the x-axis (i.e., toward the second member 226), while in other embodiments the calibration assemblies 801, 802 can be configured to extend the push rod 902a to the left along the x-axis (i.e., toward the first member 224). In other embodiments, the second calibration actuator 802 can be configured in a reverse orientation such that the push rod 902a of the calibration actuator 902 extends along the x-axis to the left (i.e., toward the first member 224).

Figure 9D:
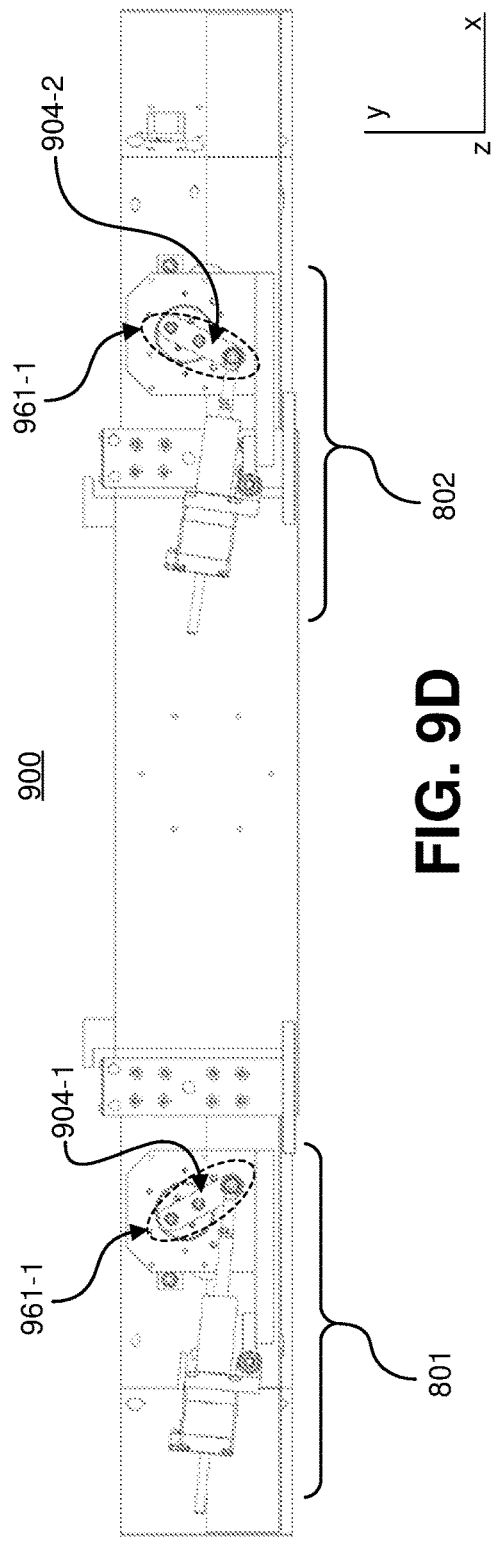
FIG. 9D illustrates the example calibration system assembly of FIG. 9C in a low state in accordance with embodiments of the technology disclosed herein.

As discussed above, the calibration system 800 is capable of moving the X-ray detector assembly 204 to account for misalignment of the fan-out beam of X-rays 208. The calibration system 800 is capable of moving the X-ray detector assembly 204 to align with the out-of-plane fan-out beam of X-rays 208. FIGS. 9D-9G illustrate positions of the calibration system assembly 900 discussed with respect to FIG. 9C. The depicted embodiments of FIGS. 9D-9G are provided for illustrative purposes only and should not be interpreted as limited to only the illustrated positioning. FIG. 9D illustrates the calibration system assembly 900 in a low state. The low state represents the lowest distance the calibration system 800 is configured to move the X-ray detector assembly 204 in the downward vertical direction (along the y-axis). In various embodiments, the low state can comprise the first lever arm 904-1 of the first calibration assembly 801 and the second lever arm 904-2 of the second calibration actuator 802 are each in a first position 961-1, 961-2 (generally, "the first positions 961," collectively, "the first position 961"). In the depicted embodiment, the first position 961-1 of the first calibration assembly 801 comprises the push rod 902a extended to contact the distal lever arm stop, and the first position 961-2 of the second calibration actuator 802 comprises the push rod 902a retracted to contact the proximal lever arm stop. The terms "distal" and "proximal" are in reference to the anchor plate 903 of the calibration assemblies 801, 802. When in the first positions 961, the X-ray detector assembly 204 is positioned at its lowest point in reference to the connecting member 206 (not shown in FIG. 9D). In this way, if the fan-out beam of X-rays 208 (not shown in FIG. 9D) intersects the X-ray detector assembly 204 below the active area, the calibration system 800 can lower the X-ray detector assembly 204 (and, accordingly, the active area 210) such that the active area 210 is aligned with the out-of-plane fan-out beam of X-rays 208.

Figure 9E:
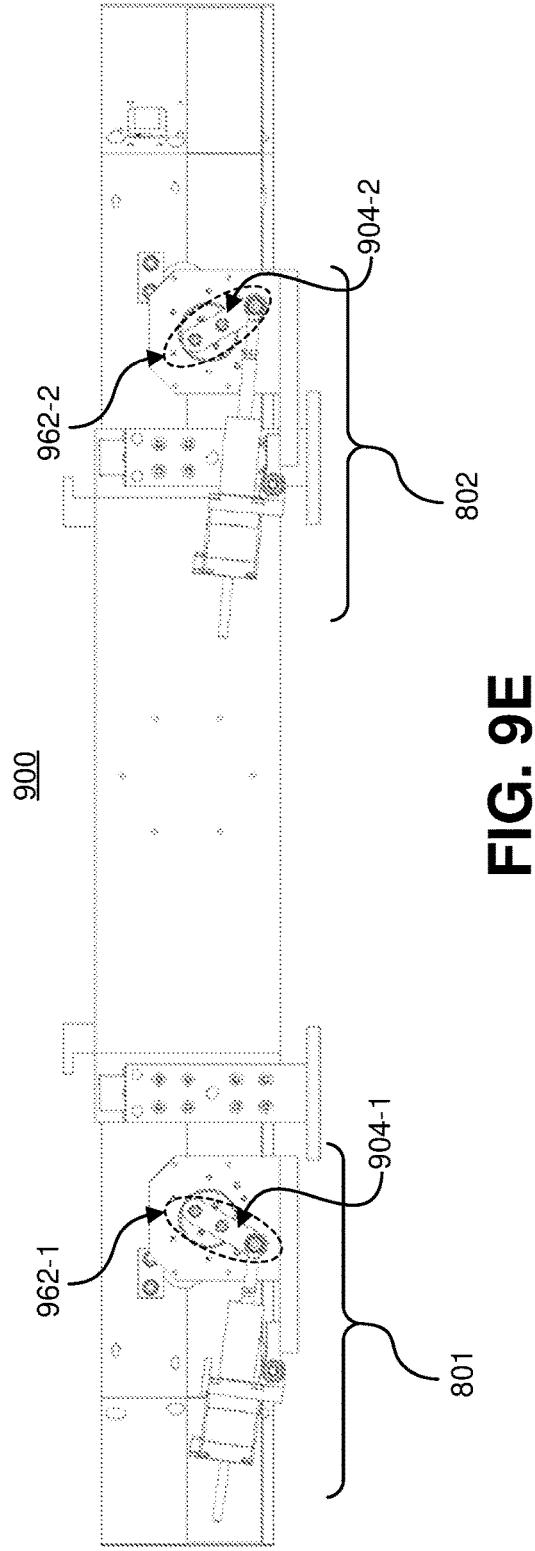
FIG. 9E illustrates the example calibration system assembly of FIG. 9C in a high state in accordance with embodiments of the technology disclosed herein.

If the fan-out beam of X-rays 208 is out-of-plane such that the beam 208 intersects the X-ray detector assembly 204 above the active area 210, the calibration system 800 can move the X-ray detector assembly in an upward vertical direction to align the active area 210 and the out-of-plane beam 208. FIG. 9E illustrates the calibration system 800 in a high state. In the high state, the calibration system 800 is configured to move the X-ray detector assembly 204 to its highest position relative to the connecting member 206. In various embodiments, the high state can comprise the first lever arm 904-1 of the first calibration assembly 801 and the second lever arm 904-2 of the second calibration actuator 802 are in a second position 962-1, 962-2 (generally, "the second positions 962," collectively, "the second position 962"). The second positions 962 can comprise each push rod 902a of the calibration assemblies 801, 802 being in the opposite state as the first positioned 961. As a non-limiting example, the push rod 902a of the first calibration assembly 801 can be retracted such that the first lever arm 904-1 contacts the proximal lever arm stop of the first calibration assembly 801.

Figure 10:
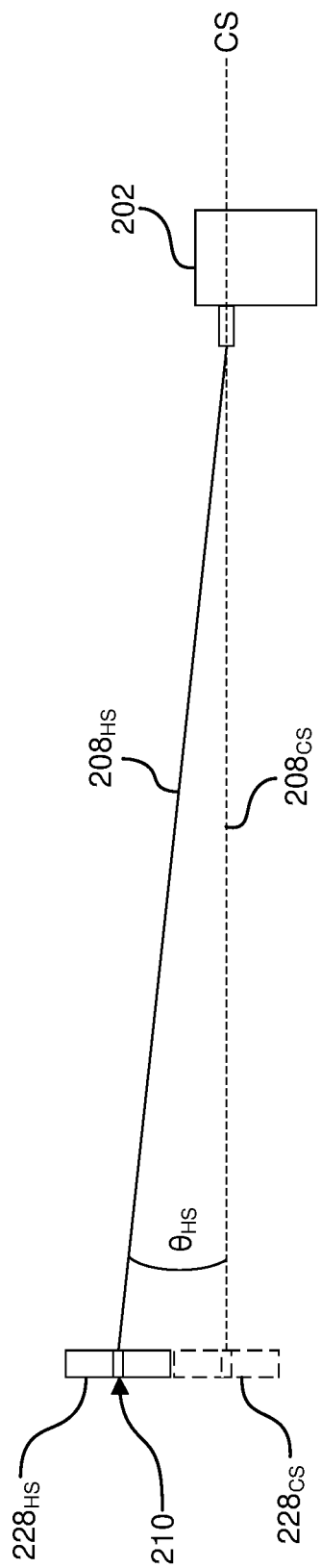
FIG. 10 illustrates an example centered state and an example high state of the calibration system assembly of FIG. 9C in accordance with embodiments of the technology disclosed herein.

In various embodiments, the calibration system assembly 900 can have a centered state where both push rod 902a of the calibration assemblies 801, 802 are extended such that the lever arms 904 are positioned at a middle point between the first and second lever arm stops of the calibration assemblies 801, 802. The middle point can be a point equidistant from the first lever arm stop and the second lever arm stop. In various embodiments, the calibration system assembly 900 can be configured such that the upward and/or downward vertical movement can be within a range of distances equivalent to a range of +/−0.1-degrees to +/−20-degrees in the pitch of the fan-out beam of X-rays 208 from the plane of the centered state. FIG. 10 illustrates the centered state and an example high state of the calibration system assembly 900 discussed with respect to FIGS. 9A-9E in accordance with embodiments of the technology disclosed herein. The example is provided for illustrative purposes only and should not be interpreted as limiting the scope of the technology disclosed to only the depicted embodiment. For ease of discussion, only the movement of the back member 228 of the X-ray detector assembly 204 is shown, and the difference in the positioning of the back member 228 is exaggerated.

As shown in FIG. 10, the centered state CS occurs where the fan-out beam of X-rays $208_{CS}$ is at a 0-degree angle (i.e., perpendicular to the back member $228_{CS}$. In the depicted example, the fan-out beam of X-rays 208 is out-of-plane with the centered state back member $228_{CS}$ in the upward vertical direction at an angle θ. In various embodiments, the angle θ can be a high-state angle $θ_{HS}$ such that the fan-out beam of X-rays $208_{HS}$ is directed above the centered state CS. In various embodiments, the high-state angle $\theta_{HS}$ can be equal to the centered state CS+0.1- to 20-degrees. The calibration system discussed with respect to FIGS. 8-9E can be configured to move the back member 228 from the centered state $228_{CS}$ to the high state $228_{HS}$, so that the high-state fan-out beam of X-rays $208_{HS}$ intersects the active area 210 of the high state back member $228_{HS}$. Where the angle θ is negative relative to the centered state CS (i.e., the angle $\theta_{LS}$), the calibration system can be configured to move the back member from the centered state $228_{CS}$ to a low state $228_{LS}$ (not shown in FIG. 10).

In various embodiments, the X-ray source 202 and the calibration system assembly 900 can operate to provide coarse and fine alignment, respectively, of the X-ray fan-out beam 208 and the active area 204 of the X-ray detector 204 to account for tolerance build up. Elements of assemblies each can have their own mechanical and/or performance tolerances. When assembled, these tolerances can cause a cumulative effect on the assembly. Such built-up tolerances can result in a cumulative effect that causes the part to fall outside of the performance levels of the assembly as designed. In various embodiments, the calibration system assembly 900 can be utilized to account for tolerance build up by allowing for fine adjustment of the X-ray detector 204 position. As a non-limiting example, the X-ray source 202 can be rotated to move the X-ray fan-out beam 208 in a vertical direction to account for variance in the vertical alignment of the X-ray source 202 and the X-ray detector 204. Due to built up tolerances, however, the rotation of the X-ray source 202 may not result in proper alignment of the X-ray fan-out beam 208 and the active area 210. The calibration system assembly 900 can be used to provide fine-grained adjustment of the positioning of the X-ray detector 204 to overcome the effect of tolerance build up.

In some embodiments, the fan-out beam of X-rays 208 can be out-of-plane through rotation around the z-axis. FIGS. 9F and 9G illustrate the tilt positions of the calibration system assembly 900 in accordance with embodiments of the technology disclosed herein. The depicted embodiments of FIGS. 9F and 9G are provided for illustrative purposes only and should not be interpreted as limiting the scope of the technology to only the depicted embodiments. As shown in FIG. 9F, in some embodiments the fan-out beam of X-rays 208 may be emitted on a tile such that a left side 981 of the beam 208 falls below the active area of the X-ray detector assembly 204, while the right side 982 of the beam 208 falls above the active area of the X-ray detector assembly 204. The left side 981 can extend from a midpoint MP of the X-ray detector assembly to a point along the negative x-axis to the left side of FIG. 9F, and the right side 982 can extend from the midpoint MP to a point along the positive x-axis to the right side of FIG. 9F. To compensate for this tilt in the fan-out beam of X-rays 208, the calibration system 800 (comprising the first calibration assembly 801 and the second calibration assembly 802) can be positioned such that the left side 981 of the X-ray detector assembly 204 is positioned below the right side 982 of the X-ray detector assembly 204.

The illustrated embodiment of FIG. 9F depicts the maximum leftward tilt of the calibration system assembly, where the first calibration assembly 801 is set at the first position 904-1 while the second calibration actuator 802 is set at the second position 962-2. In this way, the right side 982 of the X-ray detector assembly 204 is at the high state while the left side 981 of the X-ray detector assembly 204 is at the low state. Different leftward tilt positions are possible over the range of motion of the first lever arm 904-1 from the first position 961-1 to a position lesser than the position of the second lever arm 904-2. As a non-limiting example, when the second lever arm 904-2 is positioned at the centered position (i.e., equidistant from the first lever stop and the second lever stop of the second calibration actuator 802) the leftward tilt can occur over the range of the first lever arm 904-1 from the first position 961-1 to the centered point. Where the lever arm 904 are set at an equivalent corresponding position (i.e., both sides 981, 982 of the X-ray detector assembly 204 are even) then no tilt occurs. FIG. 9G illustrates the opposite situation, wherein the X-ray detector assembly 204 is in a maximum rightward tilt.

Figure 11:
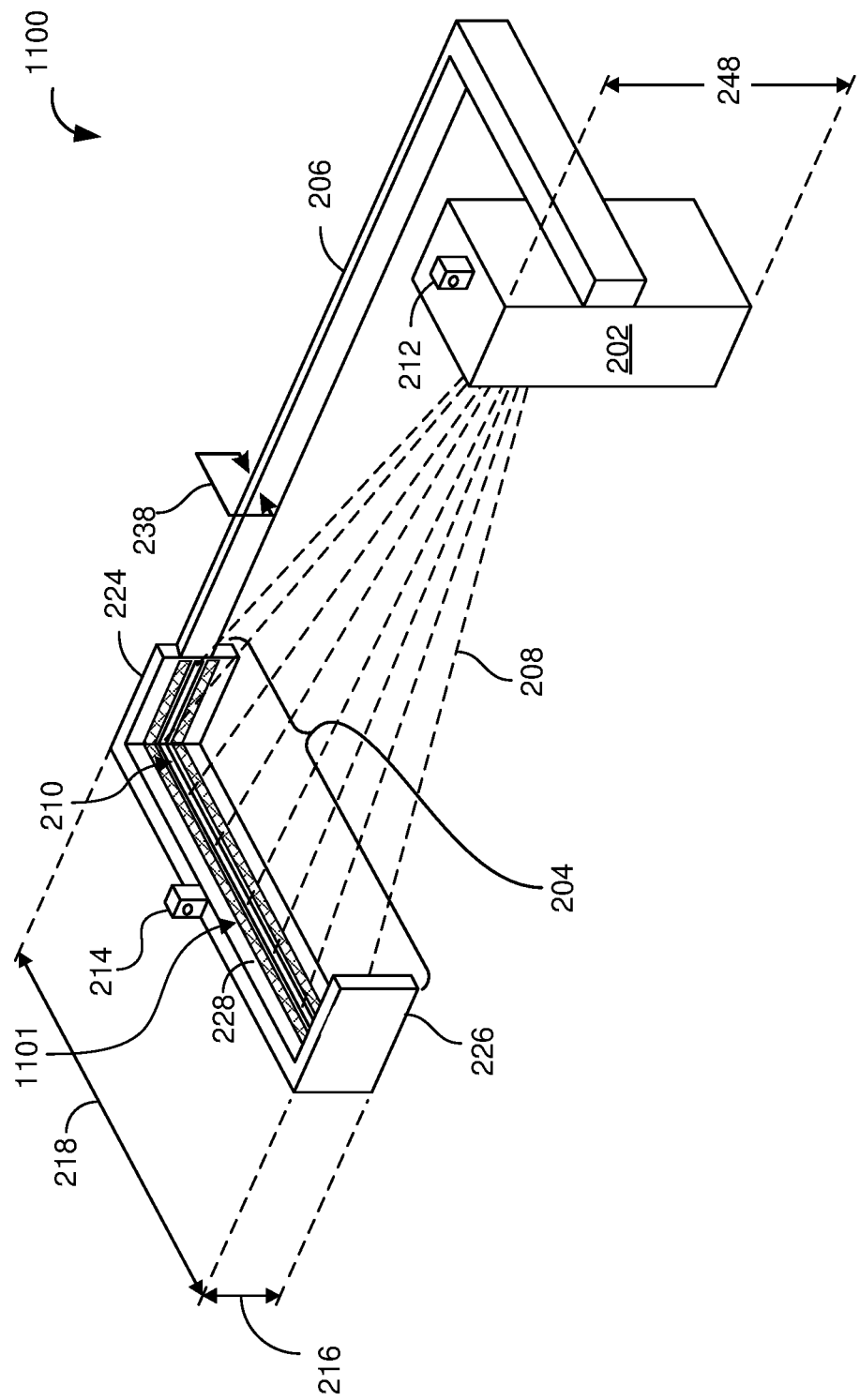
FIG. 11 illustrates another example X-ray assembly in accordance with embodiments of the technology disclosed herein.

In various embodiments, one or more sensors can be disposed on the X-ray detector assembly 204 to identify the misalignment of the fan-out beam of X-rays 208. FIG. 11 illustrates an example X-ray assembly 1100 in accordance with embodiments of the technology disclosed herein. The example X-ray assembly 100 is similar to the X-ray assembly 200 discussed with respect to FIG. 2A. Where references are common between figures it should be interpreted that the discussion of such references are applicable to all figures including those references unless expressly stated otherwise. As shown in FIG. 11, a plurality of X-ray sensors 1101 can be disposed above and below the active area 210. The plurality of X-ray sensors 1101 can be used to determine when the fan-out beam of X-rays 208 are out-of-plane with the active area 210 of the X-ray detector assembly 204. In some embodiments, the plurality of X-ray sensors 1101 can be dimensioned such that the plurality of X-ray sensors 1101 disposed above the active area can detect the position of the fan-out beam of X-rays 208 from the active area to a maximum high state and the plurality of X-ray sensors 1101 disposed below the active area can detect the position of the fan-out beam of X-rays 208 from the active area to a maximum low state, similar to the high state and low state discussed above with respect to FIGS. 9A-9G. In some embodiments, an angle sensor (not shown in FIG. 11) can be included within the X-ray assembly 1100 to sense the angle of the X-ray source 202 compared to a centered state (wherein the X-ray source 202 is configured to emit the fan-out beam of X-rays 208 at a 0-degree angle to the centered state.

Figure 12:
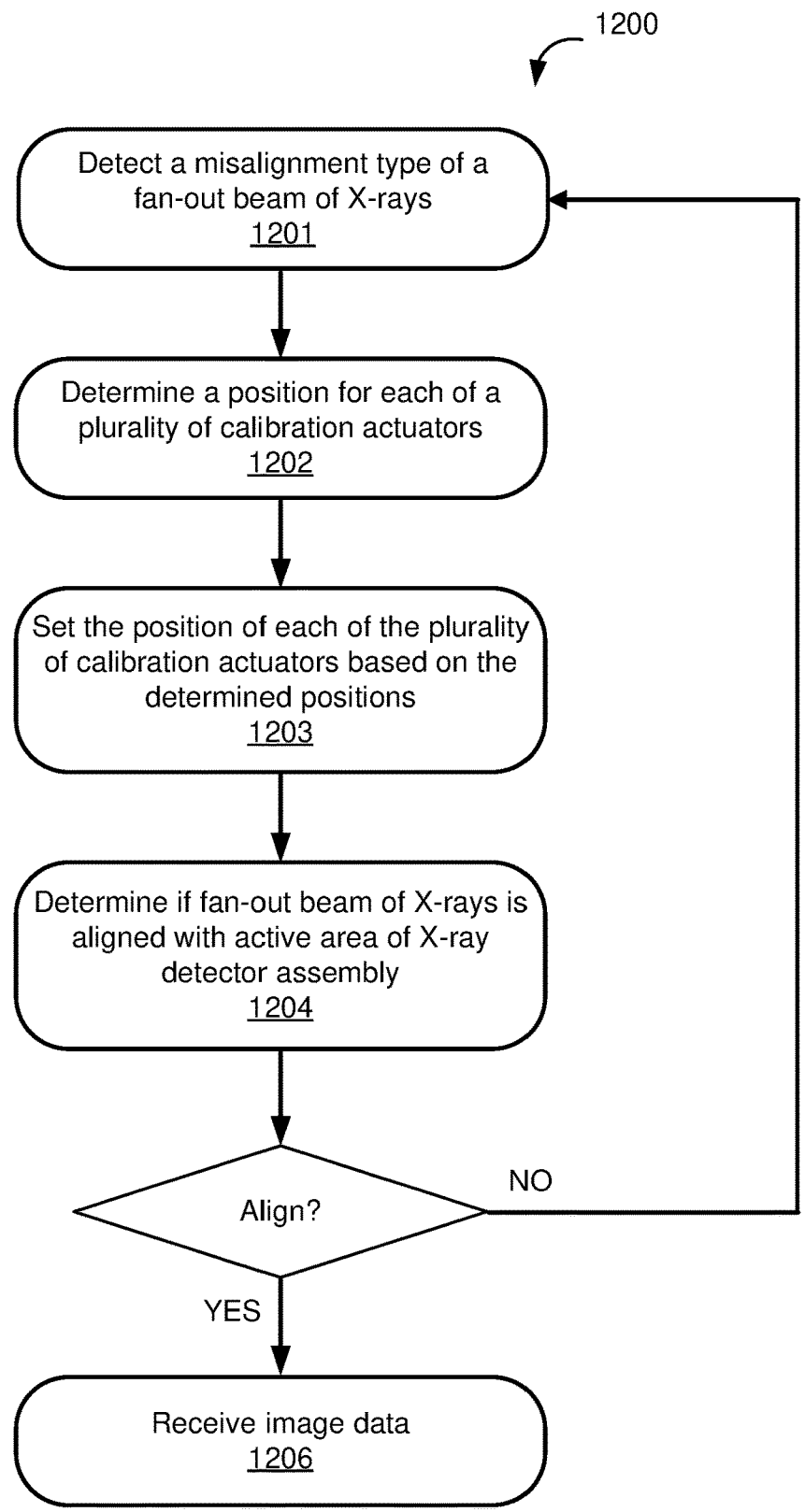
FIG. 12 is an example method in accordance with embodiments of the technology disclosed herein.

FIG. 12 illustrates an example method 1200 in accordance with embodiments of the technology disclosed herein. The example method 1200 is provided for illustrative purposes only and should not be interpreted as limiting the scope of the technology to only the depicted embodiment. In various embodiments, the method 1200 can be performed by one or more controllers communicatively coupled to the calibration system assembly 900 discussed with respect to FIGS. 9A-9G. At operation 1201, a misalignment of the fan-out beam of X-rays can be detected. In various embodiments, the detection can comprise receiving sensor data from one or more alignment sensors of the X-ray detector assembly, similar to the X-ray sensors 1101 discussed with respect to FIG. 11. In other embodiments, the misalignment can be determined based on one or more sensors configured to detect an angle of the X-ray source. The detection of a misalignment can comprise determining a type of misalignment in some embodiments. A type of misalignment can comprise an upward misalignment, a downward misalignment, a left tilt misalignment, a right tilt misalignment, or a combination thereof, similar to the misalignment discussed with respect to FIGS. 9A-9G.

At operation 1202, a corresponding position of each of a plurality of calibration actuators is determined. In various embodiments, one or more calibration actuators can be included within the calibration system assembly, each calibration actuator configured to be independently moved. The corresponding position of each of the plurality of calibration actuators is determined based on the determined misalignment type of the fan-out beam of X-rays. Based on the type of misalignment, the determined positions of the calibration actuators can be set to compensate for the type of misalignment. In various embodiments, determining the position for each of a plurality of calibration actuators comprises determining a position of a push rod of the calibration actuators to move the active area of the X-ray detector assembly to align with the fan-out beam of X-rays. In some embodiments, one or more of the calibration actuators of the plurality of calibration actuators can be positioned in a first orientation, a second orientation, or a combination thereof.

At operation 1203 the one or more controllers can set the position of each of the plurality of calibration actuators based on the determined positions of operation 1202. In various embodiments, setting the position can comprise extending a push rod of a calibration actuator to a new position corresponding to the determined position for that calibration actuator based on the type of misalignment, or retracting a push rod of a calibration actuator to a new position corresponding to the determined position for that calibration actuator.

At operation 1204, the controller can determine if the fan-out beam of X-rays is aligned with the active area of the X-ray detector assembly. When aligned, the entire length of the active area will absorb X-rays. In various embodiments, the active area can extend across the back member of the X-ray detector assembly, and the first member and second member connected at obtuse angles to the back member of the X-ray detector assembly. Misalignment can be detected when X-rays are absorbed along the entire length of the active area, and/or detected by one or more sensors disposed above and/or below the active area or at the X-ray source. If the fan-out beam of X-rays is determined to be aligned with the active area, the image data can be received at operation 1206. If the fan-out beam of X-rays is determined not to be aligned, the method can go back to operation 1201 and start the calibration process of method 1200 again. In various embodiments, the method 1200 can be performed iteratively until the misalignment is compensated for by operation of the calibration system.

Where circuits are implemented in whole or in part using software, in one embodiment, these software elements can be implemented to operate with a computing or processing system capable of carrying out the functionality described with respect thereto. One such example computing system is shown in FIG. 8. Various embodiments are described in terms of this example—computing system 800. After reading this description, it will become apparent to a person skilled in the relevant art how to implement the technology using other computing systems or architectures.

Figure 13:
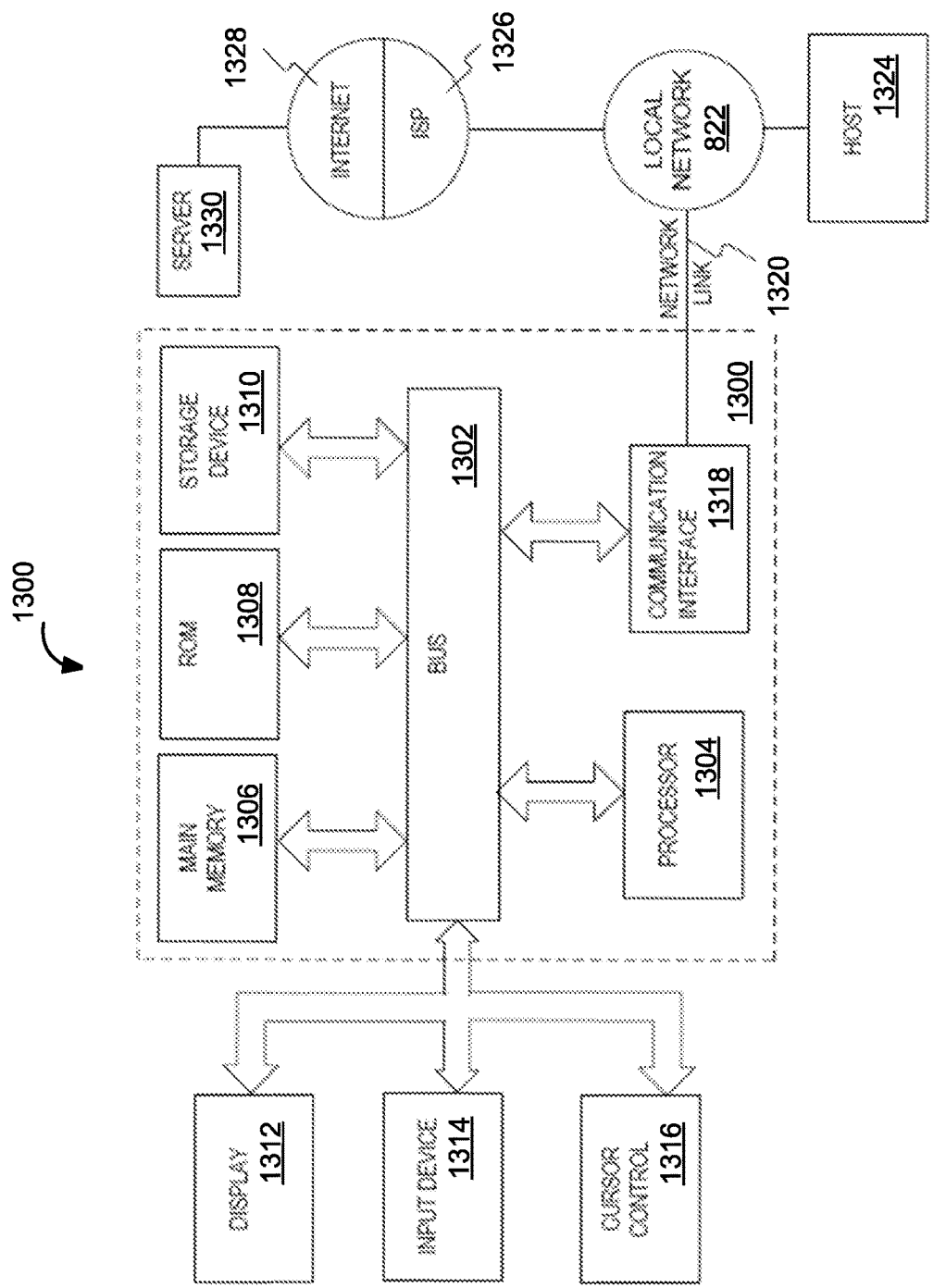
FIG. 13 illustrates an example computing system that may be used in implementing various features of embodiments of the disclosed technology.

Referring now to FIG. 13, computing system 1300 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment, such as for example, one or more of the various components illustrated in FIGS. 1-12 and described herein.

The computer system 1300 includes a bus 1302 or other communication mechanism for communicating information, one or more hardware processors 1304 coupled with bus 1302 for processing information. Hardware processor(s) 1304 may be, for example, one or more general purpose microprocessors. The computer system 1300 also includes a main memory 1308, such as a random access memory (RAM), cache and/or other dynamic storage devices, coupled to bus 1302 for storing information and instructions to be executed by processor 130404. Main memory 1308 also may be used for storing temporary variables or other intermediate information during execution of instructions to be executed by processor 1304. Such instructions, when stored in storage media accessible to processor 1304, render computer system 1300 into a special-purpose machine that is customized to perform the operations specified in the instructions.

The computer system 1300 further includes a read only memory (ROM) 1308 or other static storage device coupled to bus 1302 for storing static information and instructions for processor 1304. A storage device 1310, such as a magnetic disk, optical disk, or USB thumb drive (Flash drive), etc., is provided and coupled to bus 1302 for storing information and instructions.

The computer system 1300 may be coupled via bus 1302 to a display 1312, such as a cathode ray tube (CRT) or LCD display (or touch screen), for displaying information to a computer user. An input device 1314, including alphanumeric and other keys, is coupled to bus 1302 for communicating information and command selections to processor 1304. Another type of user input device is cursor control 1318, such as a mouse, a trackball, or cursor direction keys for communicating direction information and command selections to processor 1304 and for controlling cursor movement on display 1312. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

The computing system 1300 may include a user interface component to implement a GUI that may be stored in a mass storage device as executable software codes that are executed by the computing device(s). This and other components may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computer system 1300 may implement the techniques described herein using customized hard-wired logic, one or more ASICs or FPGAs, firmware and/or program logic which in combination with the computer system causes or programs computer system 1300 to be a special-purpose machine. According to one embodiment, the techniques herein are performed by computer system 1300 in response to processor(s) 1304 executing one or more sequences of one or more instructions contained in main memory 1308. Such instructions may be read into main memory 1308 from another storage medium. Execution of the sequences of instructions contained in main memory 1308 causes processor(s) 1304 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks. Volatile media includes dynamic memory, such as main memory 1308. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1302. Transmission media can also take the form of acoustic or light waves, such as those generated during radio-wave and infra-red data communications.

Various forms of media may be involved in carrying one or more sequences of one or more instructions to processor 1304 for execution. For example, the instructions may initially be carried on a magnetic disk or solid state drive of a remote computer. The remote computer can load the instructions into its dynamic memory and send the instructions over a telephone line using a modem. A modem local to computer system 1300 can receive the data on the telephone line and use an infra-red transmitter to convert the data to an infra-red signal. An infra-red detector can receive the data carried in the infra-red signal and appropriate circuitry can place the data on bus 1302. Bus 1302 carries the data to main memory 1308, from which processor 1304 retrieves and executes the instructions. The instructions received by main memory 1308 may retrieves and executes the instructions. The instructions received by main memory 1308 may optionally be stored on a storage device either before or after execution by processor 1304.

The computer system 1300 also includes a communication interface 1318 coupled to bus 1302. Communication interface 1318 provides a two-way data communication coupling to one or more network links that are connected to one or more local networks. For example, communication interface 1318 may be an integrated services digital network (ISDN) card, cable modem, satellite modem, or a modem to provide a data communication connection to a corresponding type of telephone line. As another example, network interface 1318 may be a local area network (LAN) card to provide a data communication connection to a compatible LAN (or WAN component to communicated with a WAN). Wireless links may also be implemented. In any such implementation, network interface 1318 sends and receives electrical, electromagnetic or optical signals that carry digital data streams representing various types of information.

A network link 1320 typically provides data communication through one or more networks to other data devices. For example, a network link may provide a connection through local network to a host computer 1324 or to data equipment operated by an Internet Service Provider (ISP) 1328. The ISP 1328 in turn provides data communication services through the world wide packet data communication network now commonly referred to as the "Internet" 1328. Local network 1322 and Internet 1328 both use electrical, electromagnetic or optical signals that carry digital data streams. The signals through the various networks and the signals on network link and through communication interface 1318, which carry the digital data to and from computer system 1300, are example forms of transmission media.

The computer system 1300 can send messages and receive data, including program code, through the network(s), network link and communication interface 1318. In the Internet example, a server 1330 might transmit a requested code for an application program through the Internet 1328, the ISP 1328, the local network 1322 and the communication interface 1318.

The received code may be executed by processor 1304 as it is received, and/or stored in storage device 1310, or other non-volatile storage for later execution.

Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system comprising:
   an X-ray source configured to emit an X-ray fan beam;
   an X-ray detector configured to detect the X-ray fan beam;
   a connecting member connecting the X-ray source and the X-ray detector such that the X-ray source and X-ray detector remain in geometric alignment for the X-ray detector to detect the X-ray fan beam;
   a base frame encompassing a base compartment, the base frame comprising an upper surface for a person to stand upon during imaging, wherein a portion of the X-ray fan beam passes through a portion of the base compartment during imaging;
   a source-side frame encompassing a source-side compartment containing the X-ray source, wherein the source-side frame is attached to a first end of the base frame;
   a detector-side frame encompassing a detector-side compartment containing a portion of the X-ray detector, the detector-side frame attached to a second end of the base frame such that a portion of the X-ray fan beam passes through the person during imaging;
   a connecting frame encompassing a connecting compartment containing a portion of the connecting member, wherein the connecting frame is attached to the source-side frame and the detector-side frame;
   an actuator for moving the X-ray fan beam over the person during imaging; and
   a computer configured to receive X-ray data from the X-ray detector and produce a digital image of the person from the received X-ray data.

2. The system of claim 1, wherein a portion of the X-ray fan beam passes through a portion of the connecting compartment during imaging.

3. The system of claim 1, wherein the base compartment contains a portion of the connecting member during imaging.

4. The system of claim 1, wherein a portion of the X-ray fan beam passes through a portion of the base compartment and a portion of the connecting compartment during imaging.

5. The system of claim 4, wherein the base compartment contains a portion of the connecting member during imaging.

6. The system of claim 1, further comprising a first calibration assembly operatively connected to the X-ray detector.

7. The system of claim 1, further comprising a controller configured to receive a user input to initiate the imaging process.

8. The system of claim 1, wherein moving the X-ray fan beam comprises translating the X-ray detector and translating the X-ray source, wherein the translation of the X-ray detector is greater than the translation of the X-ray source.

9. The system of claim 1, wherein the actuator comprises a rotational actuator.

10. An imaging assembly comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging, wherein the base compartment contains a portion of the connecting member during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame, wherein a portion of the X-ray fan beam passes through a portion of the base compartment and a portion of the connecting compartment during imaging; and
an actuator for moving the X-ray fan beam over the person during imaging.

11. The imaging assembly of claim 10, further comprising a computer configured to receive X-ray data from the X-ray detector, generate a digital image of the person from the received X-ray data, and store the digital image.

12. The imaging assembly of claim 11, wherein the connecting frame is attached to the base frame.

13. The imaging assembly of claim 11, wherein moving the X-ray fan beam comprises translating the X-ray detector and translating the X-ray source, wherein the translation of the X-ray detector is greater than the translation of the X-ray source.

14. The imaging assembly of claim 13, wherein the actuator comprises a first linear actuator for translating the X-ray detector and a second linear actuator for translating the X-ray source.

15. The imaging assembly of claim 14, wherein the first linear actuator is configured to effectuate vertical translation of the X-ray source, and wherein the second linear actuator is configured to effectuate vertical translation of the X-ray detector.

16. The imaging assembly of claim 14, wherein the X-ray source is translated at a first rate and the X-ray detector is translated at a second rate.

17. The imaging assembly of claim 13, wherein the actuator comprises a rotational actuator, wherein rotation of the rotational actuator corresponds to the translation of the X-ray detector.

18. The imaging assembly of claim 13, wherein translation of the X-ray detector and the translation of the X-ray source comprises a rotation of the connecting member.

19. The imaging assembly of claim 18, wherein the axis of rotation of the connecting member is farther from the X-ray detector than the X-ray source.

20. A system comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame, and wherein a portion of the X-ray fan beam passes through a portion of the connecting compartment during imaging;
an actuator for moving the X-ray fan beam over the person during imaging; and
a computer configured to receive X-ray data from the X-ray detector and produce a digital image of the person from the received X-ray data.

21. A system comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging, and wherein the base compartment contains a portion of the connecting member during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame;
an actuator for moving the X-ray fan beam over the person during imaging; and
a computer configured to receive X-ray data from the X-ray detector and produce a digital image of the person from the received X-ray data.

22. A system comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame, wherein a portion of the X-ray fan beam passes through a portion of the base compartment and a portion of the connecting compartment during imaging;
an actuator for moving the X-ray fan beam over the person during imaging; and
a computer configured to receive X-ray data from the X-ray detector and produce a digital image of the person from the received X-ray data.

23. A system comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging, wherein the base compartment contains a portion of the connecting member during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame;
an actuator for moving the X-ray fan beam over the person during imaging; and
a computer configured to receive X-ray data from the X-ray detector and produce a digital image of the person from the received X-ray data.

24. A system comprising:
an X-ray source configured to emit an X-ray fan beam;
an X-ray detector configured to detect the X-ray fan beam;
a connecting member connecting the X-ray source and the X-ray detector such that the X-ray source and X-ray detector remain in geometric alignment for the X-ray detector to detect the X-ray fan beam;
a base frame encompassing a base compartment, the base frame comprising an upper surface for a person to stand upon during imaging;
a source-side frame encompassing a source-side compartment containing the X-ray source, wherein the source-side frame is attached to a first end of the base frame;
a detector-side frame encompassing a detector-side compartment containing a portion of the X-ray detector, the detector-side frame attached to a second end of the base frame such that a portion of the X-ray fan beam passes through the person during imaging;
a connecting frame encompassing a connecting compartment containing a portion of the connecting member, wherein the connecting frame is attached to the source-side frame and the detector-side frame;
an actuator for moving the X-ray fan beam over the person during imaging, wherein moving the X-ray fan beam comprises translating the X-ray detector and translating the X-ray source, wherein the translation of the X-ray detector is greater than the translation of the X-ray source; and
a computer configured to receive X-ray data from the X-ray detector and produce a digital image of the person from the received X-ray data.

* * * * *